US008492362B1

(12) United States Patent
Chu

(10) Patent No.: US 8,492,362 B1
(45) Date of Patent: Jul. 23, 2013

(54) 5-(*E*)-BROMOVINYL URACIL ANALOGUES AND RELATED PYRIMIDINE NUCLEOSIDES AS ANTI-VARICELLA ZOSTER VIRUS AGENTS AND METHODS OF USE

(75) Inventor: Chung K. Chu, Stratham, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 76 days.

(21) Appl. No.: 13/291,512

(22) Filed: Nov. 8, 2011

(51) Int. Cl.
*A01N 43/04* (2006.01)
*A61K 31/70* (2006.01)

(52) U.S. Cl.
USPC .................. 514/51; 514/43; 514/49; 514/50; 536/26.1; 536/28.1; 536/28.4; 536/28.53

(58) Field of Classification Search
None
See application file for complete search history.

(56) References Cited

PUBLICATIONS

Afouna, M. I., Mehta, S. C., Ghanem, A. H., Higuchi, W. I., Kern, E. R., De Clercq, E., and El-Shattawy, H. H. (1998). Assessment of correlation between skin target site free drug concentration and the in vivo topical antiviral efficacy in hairless mice for (E)-5-(2-bromovinyl)-2'-deoxyuridine and acyclovir formulations. J Pharm Sci 87(8), 917-21.
Ahmed, A. M., Brantley, J. S., Madkan, V., Medoza, N., and Tyring, S. K. (2007). Managing herpes zoster in immunocompromised patients. Herpes 14(2), 32-6.
Andrei, G., Snoeck, R., Reymen, D., Liesnard, C., Goubau, P., Desmyter, J., and De Clercq, E. (1995). Comparative activity of selected antiviral compounds agai̇nist clinical isolates of varicella-zoster virus. Eur J Clin Mircobiol Infect Dis 14(4), 318-29.
Babich, H., Sedletcaia, A., and Kenigsberg, B. (2002). In vitro cytotoxicity of protocatechuic acid and cultured human cells from oral tissue: involvement in oxidative stress. Pharmacol Toxicol 91(5), 245-33.
Balzarini, J., Bohman, C., and De Clercq, E. (1993). Differential mechanism of cytostatic effect of (E)-5-(2-bromovinyl)-2'-deoxyuridine, 9-(1,3-dihydroxyl-2-propoxymethyl)guanine, and other antiherpetic drugs on tumor cells transfected by the thymidine kinase gene of herpes simplex virus type 1 or type 2. J Biol Chem 268(9), 6332-7.
Bednarski, K., Dixit, D., Wang, W., Evans, C., Jin, H., Yuen, L., and Mansour, T. (1994). Inhibitory activities of herpes simplex viruses type 1 and 2 and human cytomegalovirus by stereoisomers of 2'-deoxy-3'oxa-5(E)-2-bromovinyl) uridines and their 4'-thio analogues. Bioorg Med Chem Lett 4(22), 2667-2672.
Choi, Y., Li, L., Grill, S., Gullen, E., Lee, C. S., Gumina, G., Tsujii, E., Cheng, Y. C., and Chu, C. K. (2000). Structure-activity relationships of (E)-5-(2-bromovinyl)uracil and related pyrimidine nucleosides as antiviral agents for herpes viruses. J Med Chem 43(13), 2538-46.
Chu, C. K., Ma, T., Shanmuganathan, K., Wang, C., Xiang, Y., Pai, S. B., Yao, G. Q., Sommadossi, J. P., and Cheng, Y. C. (1995). Use of 2'-fluoro-5-methyl-beta-L-arbinofuranosyluracil as a novel antiviral agent for hepatitis B virus and Epstein-Barr virus. Antimicrob Agents Chemother 39(4), 979-81.
Cohen, J. I., Straus, S. E., and Arvin, A. M. (2007). Varicella-zoster virus replication, pathogenesis, and management. 5th ed. In "Fields Virology" (D.M. Knipe, P. M. Howley, D. E. Griffin, R. A. Lamb, M. A. Martin, B. Roizman, and S. E. Straus, Eds.), vol. 2, pp. 2773-2818. 2 vols. Lippincott-Williams and Wilkens, Philadelphia.
De Clercq, E., Descamps, J., De Somer, P., Barr, P. J., Jones, A. S., and Walker, R. T. (1979). (E)-5-(2-Bromovinyl)-2'-deoxyuridine: a potent and selective anti-herpes agent. Proc Natl Acad Sci U S A 76(6), 2947-51.
De Clercq, E. (2004). Antiviral drugs in current clinical use. J Clin Virol 30(2), 115-33.
De Clercq, E. (2005). Recent highlights in the development of new antiviral drugs. Current Opinion in Microbiology 8 (5), 552-60.
Diasio, R. B. (1998). Sorivudine and 5-fluorouracil; a clinically significant drug-drug interaction due to inhibition of dihydropyrimidine dehydrogenase. Br J Clin Pharmacol 46(1), 1-4.
Eisfeld, A. J., Turse, S. E., Jackson, S. A., Lemer, E. C., and Kinchington, P. R. (2006). Phosphorylation of the varicella-zoster virus (VZV) major transcriptional regulatory protein IE62 by the VZV open reading frame 66 protein kinase. J Virol 80(4), 1710-23.
Holcomb, K., and Weinberg, J. M. (2006). A novel vaccine (Zostavax) to prevent herpes zoster and postherpetic neuralgia. J Drugs Dermatol 5(9), 863-6.
Keam, S. J., Chapman, T. M., and Figgitt, D. P. (2004). Brivudin (bromovinyl deoxyuridine). Drugs 64(18), 2091-7; discussion 2098-9.
Keizer, H. J., De Bruijn, E. A., Tjaden, U. R., and De Clercq, E. (1994). Inhibition of fluorouracil catabolism in cancer patients by the antiviral agent (E)-5-(2-bromovinyl)-2'-deoxyuridine. J Cancer Res Clin Oncol 120(9), 545-9.
Kinchington, P. R., and Turse, S. E. (1998). Regulated nuclear localization of the varicella-zoster virus major regulatory protein, IE62. J Infect Dis 178 Suppl 1, S16-21.
Kinchington, P. R., Fite, K., and Turse, S. E. (2000). Nuclear Accumulation of IE62, the Varicella-Zoster Virus (VZV) Major Transcriptional Regulatory Protein, Is Inhibited by Phosphorylation Mediated by the VZV Open Reading Frame 66 Protein Kinase. J. Virol. 74(5), 2265-2277.
Ku, C. C., Zerboni, L., Ito, H., Graham, B. S., Wallace, M., and Arvin, A. M. (2004). Varicella-zoster virus transfer to skin by T Cells and modulation of viral replication by epidermal cell interferon-alpha. J Exp Med 200(7), 917-25.
Leisenfelder, S. A., and Moffat, J. F. (2006). Varicella-zoster virus infection of human foreskin fibroblast cells results in atypical cyclin expression and cyclin-dependent kinase activity. J Virol 80(11), 5577-87.
Li, L., Dutschman, G. E., Gullen, E. A., Tsujii, E., Grill, S. P., Choi, Y., Chu, C. K., and Cheng, Y. C. (2000). Metabolism and mode of inhibition of varicella-zoster virus by L-beta-5-bromovinyl-(2-hydroxymethyl)-(1,3-dioxolanyl)uracil is dependent on viral thymidine kinase. Mol Pharmacol 58(5), 1109-14.
Moffat, J. F., Stein, M. D., Kaneshima, H., and Arvin, A. M. (1995). Tropsim of varicella-zoster virus for human CD4+ and CD8+ T lymphocytes and epidermal cells in SCID-hu mice. Journal of Virology 69(9), 5236-42.

(Continued)

*Primary Examiner* — Patrick Lewis
(74) *Attorney, Agent, or Firm* — Henry D. Coleman; R. Neil Sudol

(57) ABSTRACT

The present invention relates to prodrug forms of β-L-1-[5-(E-2-Bromovinyl)-2-(hydroxymethyl)-1,3-dioxolan-4-yl)] uracil (L-BHDU) and their use to treat viral infections of Varicella Zoster Virus, including recurrent VZV (shingles), especially including drug resistant Varicella Zoster Virus and related complications of this viral infection such as rash or post-herpetic neuralgia.

23 Claims, 6 Drawing Sheets

PUBLICATIONS

Figure 1:
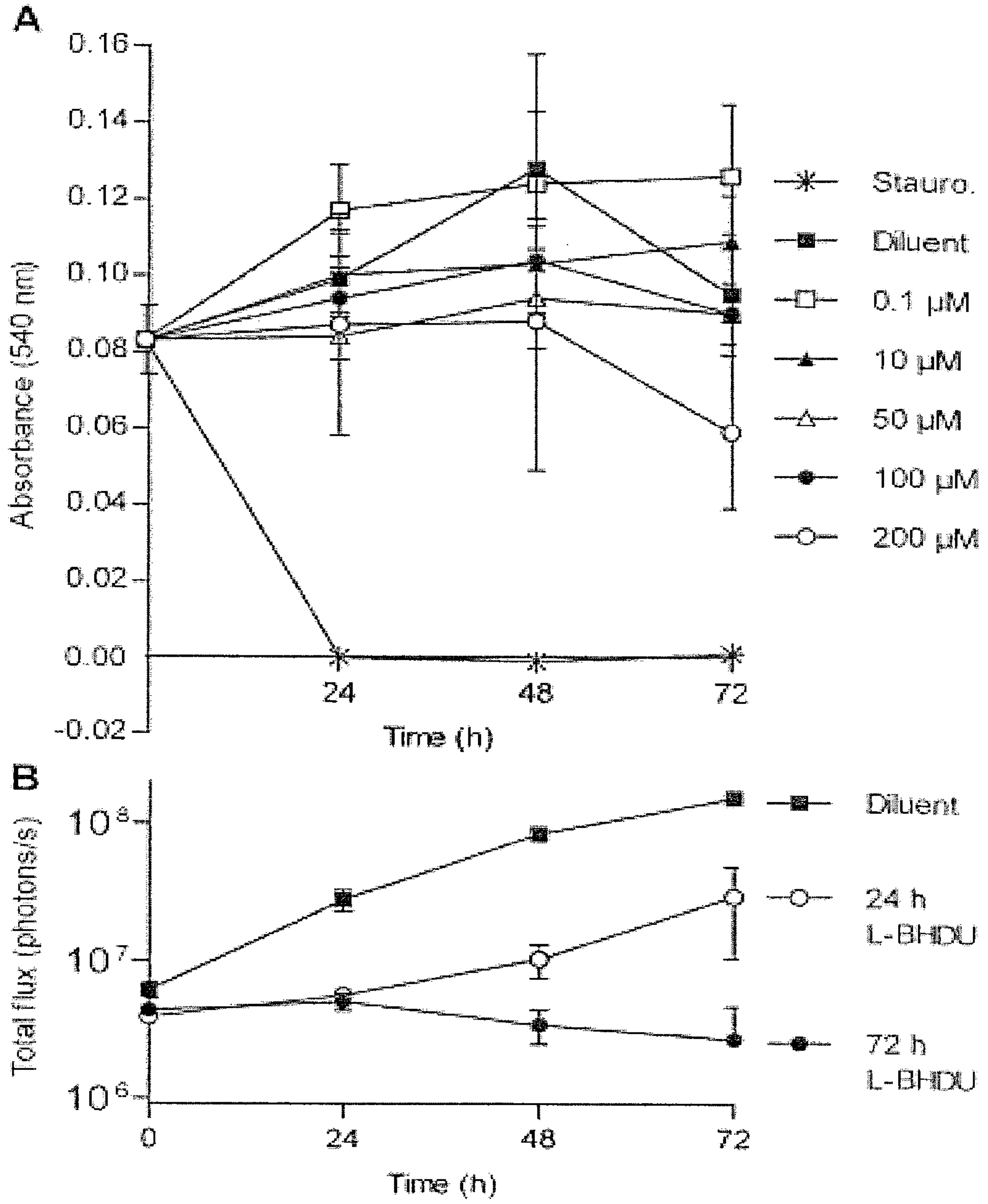

Moffat, J. F., and Arvin, A. M. (1999). Varicella-zoster virus infection of T cells and skin in the SCID-hu mouse model. In "Handbook of Animal Models of Infection" (O. Zak, and M. A. Sande, Eds.), pp. 973-980. Academic Press, San Diego.

Oliver, S. L., Zerboni, L., Sommer, M., Rajamani, J., and Arvin, A. M. (2008). Development of recombinant varicella-zoster viruses expressing luciferase fusion proteins for live in vivo imaging in human skin and dorsal root ganglia xengrafts. J Virol Methods 154(1-2), 182-93.

Oxman, M. N., et al. (2005). A vaccine to prevent herpes zoster and postherpetic neuralgia in older adults. N Engl J Med 352(22), 2271-84.

Perera, L. P., Mosca, J. D., Sadeghi-Zadeh, M., Ruyechan, W. T., and Hay, J. (1992). The varicella-zoster virus immediate early protein, IE62, can positively regulate it cognate promoter. Virology 191(1), 346-54.

Piette, J., Defechereux, P., Baudoux, L., Debrus, S., Merville, M. P., and Rentier, B. (1995). Varicella-zoster virus gene regulation. Neurology 45(Suppl 8), S23-7.

Repetto, G., del Peso, A., and Zurita, J. L. (2008). Neural red uptake assay for the estimation of cell viability/cytotoxicity. Nat Protoc 3(7), 1125-31.

Rowe, J., Greenblatt, R. J., Liu, D., and Moffat, J. F. (2010) Compounds that target host cell proteins prevent varicella-zoster virus replication in culture, ex vivo, and in SCID-Hu mice. Antiviral Res. 86, 276-285.

Sampathkumar, P., Drage, L. A., and Martin, D. P. (2009). Herpes zoster (shingles) and prostherpetic neuralgia. Mayo Clin Proc 84(3), 274-80.

Seward, J. F., Marin, M., and Vazquez, M. (2008). Varicella vaccine effectiveness in the US vaccination program: a review. J Infect Dis 197 Suppl 2, S82-9.

Sexton, C. J., Navsaria, H. A., Leigh, I. M., and Powell, K. (1992). Replication of varicella zoster virus in primary human keratinocytes. J Med Virol 38(4), 260-4.

Shigeta, S., Yokota, T., Iwabuchi, T., Baba, M., Konno, K., Ogata, M., and De Clercq, E. (1983). Comparative efficacy of antiherpes drugs against various strains of varicella-zoster virus. J Infect Dis 147(3), 576-84.

Spadari, S., Maga, G., Focher, F., Ciarrocchi, G., Manservigi, R., Arcamone, F., Capobianco, M., Carcuro, A., Colonna, F., Iotti, S., and et al. (1992). L-thymidine is phosphorylated by herpes simplex virus type 1 thymidine kinase and inhibits viral growth. J Med Chem 35(22), 4214-20.

Taylor, S. L., Kinchington, P. R., Brooks, A., and Moffat, J. F. (2004). Roscovitine, a cyclin dependent kinase inhibitor, prevents replication of varicella-zoster virus. Journal of Virology 78(6), 2853-2862.

Taylor, S. L., and Moffat, J. F. (2005). Replication of varicella-zoster virus in human skin organ culture. J Virol 79(17), 11501-6.

Vazquez, M., LaRussa, P. S., Gershon, A. A., Niccolai, L. M., Muehlenbein, C. E., Steinberg, S. P., and Shapiro, E. D. (2004). Effectiveness over time of varicella vaccine. Jama 291(7), 851-5.

Zhang, Z., Rowe, J., Wang, W., Sommer, M., Arvin, A., Moffat, J., and Zhu, H. (2007). Genetic analysis of varicella-zoster virus ORF0 to ORF4 by use of a novel luciferase bacterial artificial chromosome system. J Virol 81(17), 9024-33.

FIGURE 5

Table 1

| Treatment | Dose | ABWD[a] | Mortality | Avg. VZV Growth Rate[b] | SD[c] | p value[c] |
|---|---|---|---|---|---|---|
| DMSO | 50% DMSO | -5.05 | 1/8 | 0.61 | 0.10 | - |
| VACV | 3 mg/mL in drinking water | -6.30 | 0/5 | 0.62 | 0.05 | 1.000 |
| L-BHDU | 8 mg/kg/day | -2.92 | 1/5 | 0.24 | 0.17 | 0.004 |
| L-BHDU | 15 mg/kg/day | -4.33 | 0/5 | 0.25 | 0.09 | 0.002 |
| L-BHDU | 150 mg/kg/day | -1.46 | 0/5 | 0.09 | 0.21 | 0.002 |

[a] Average Body Weight Difference (weight at Day 8 post infection minus weight at Day 0 post infection)

[b] VZV growth rate ($log_{10}$ photons/s/day).

[c] ±SD and p values determined using the Mann-Whitney U two-tailed test.

FIGURE 6

Table 2. Mean (± SD) L-BHDU two hours post final treatment

| Parameter | 150 mg/kg/day (n = 5) | Ratio to Plasma | 8 mg/kg/day (n = 4) | Ratio to Plasma |
|---|---|---|---|---|
| Cmax, µg/ml or µg/g | | | | |
| Plasma | 13.85 (3.93) | - | 0.34 (0.20) | - |
| Brain | 1.11 (0.34) | 0.08 (0.03) | 0.12 (0.02) | 0.36 (0.26) |
| Skin-Hu | 11.34 (1.12) | 0.88 (0.29) | 0.73 (0.08) | 3.14 (2.61) |
| Skin-Mu | 11.79 (0.96) | 0.89 (0.20) | 0.69 (0.08) | 2.98 (2.54) |
| Heart | 13.71 (2.81) | 1.01 (0.16) | 0.67 (0.12) | 2.87 (2.56) |
| Spleen | 18.81 (6.20) | 1.36 (0.23) | 0.55 (0.16) | 2.12 (1.26) |
| Liver | 19.76 (4.08) | 1.47 (0.30) | 1.38 (0.54) | 4.48 (1.14) |
| Kidney | 27.41 (3.53) | 2.05 (0.35) | 1.30 (0.24) | 5.11 (3.09) |
| Lung | 30.39 (2.77) | 2.29 (0.45) | 3.00 (0.77) | 11.22 (5.67) |

5-(*E*)-BROMOVINYL URACIL ANALOGUES AND RELATED PYRIMIDINE NUCLEOSIDES AS ANTI-VARICELLA ZOSTER VIRUS AGENTS AND METHODS OF USE

FIELD OF THE INVENTION

The present invention relates to prodrug forms of pyrimidine nucleoside compounds, in particular, β-L-1-[5-(E-2-Bromovinyl)-2-(hydroxymethyl)-1,3-dioxolan-4-yl)]uracil (L-BHDU) and their use to treat viral infections of Varicella Zoster Virus, including recurrent VZV (shingles), especially including drug resistant Varicella Zoster Virus and related complications of this viral infection such as skin rash or post-herpetic neuralgia.

BACKGROUND OF THE INVENTION

Varicella-zoster virus (VZV) is a human-restricted alphaherpesvirus. It causes varicella (chicken pox) upon primary infection and zoster (shingles) upon reactivation from latency. VZV disease is partially preventable by inoculation with the live, attenuated vaccine strain Oka-Merck (Oxman et al., 2005; Vazquez et al., 2004). Pediatric vaccination has reduced varicella cases in the United States (Seward et al., 2008), although the incidence of zoster is not likely to decline in the near future because in older adults the vaccine efficacy is approximately 50% (Holcomb and Weinberg, 2006). There will continue to be a demand for antiviral drugs for VZV due to natural and breakthrough cases and in immunocompromised patients that cannot receive live virus vaccines. Current treatments are nucleoside and pyrophosphate analogues that target the virus DNA polymerase and may depend on virus thymidine kinase activity (De Clercq, 2004). Acyclovir (ACV) and its derivatives valaciclovir (VACV), penciclovir (PCV) and famciclovir (FCV) are acyclic derivatives of guanine. They are moderately effective against VZV, but for best results treatment should begin within 72 h of rash onset and resistance may arise during long-term administration to immunocompromised patients (Sampathkumar et al., 2009). In these patients, Foscarnet (phosphonoformate) delivered intravenously may be necessary to treat resistant VZV (Ahmed et al., 2007). These drugs are widely approved for use in the United States, Europe, and Asia.

The cyclic derivatives of uridine are another class of drugs currently used to treat VZV. Infections in the eye (herpes zoster ophthalmicus) can be treated with topical idoxuridine and trifluridine. Brivudin [BVDU, (E)-5-(2-bromovinyl)-2'-deoxyuridine] is approved for use in Europe and was the first bromovinyl nucleoside analog to show anti-herpesvirus activity (De Clercq et al., 1979). BVDU is phosphorylated by the virus-encoded thymidine kinase (TK) to both the 5'-monophosphate and 5'-diphosphate forms. Cellular kinases produce the 5'-triphosphate form (BVDU-TP). BVDU-TP interacts with the viral DNA polymerase either as a competitive inhibitor or an alternative substrate whereby it can be incorporated into the DNA chain (reviewed in (De Clercq, 2005)). BVDU is more potent against VZV than acyclovir and its derivatives (Andrei et al., 1995; Shigeta et al., 1983). Another benefit of BVDU over acyclovir is the ease of dosing, making it appealing to elderly patients (De Clercq, 2005). The main drawback of BVDU is that it is cleaved into a metabolite of BVU. BVU in turn inhibits dihydropyrimidine dehydrogenase, which is involved in the degradation of thymidine, uracil, and the commonly used cancer drug 5'-fluorouracil (5-FU). Patients receiving this chemotherapy regimen should not be given BVDU as it may cause toxic accumulation of 5-FU and result in death [reviewed in (De Clercq, 2004; De Clercq, 2005; Diasio, 1998; Keizer et al., 1994)].

The serious possible adverse effects of BVDU are the main reason why related compounds have been screened for antiviral activity without the potential toxicity. One approach has been to screen nucleosides in the non-naturally occurring L-configuration, which can be just as effective as the D-nucleoside counterparts (Chu et al., 1995; Spadari et al., 1992). The uridine derivative, β-L-1-[5-(E-2-Bromovinyl)-2-(hydroxymethyl)-1,3-dioxolan-4-yl)]uracil (L-BHDU), exhibited potent anti-VZV activity in cultured cells and it was noncytotoxic in HEL 299 cells up to 200 μM (Choi et al., 2000; Li et al., 2000). Efforts to elucidate the mechanism of action found that L-BHDU was phosphorylated by VZV TK but not further converted to the di- and triphosphate forms. This is different from BVDU and implies an alternative antiviral mechanism (Li et al., 2000). Their evidence pointed to the monophosphate form as the active moiety that would inhibit VZV DNA polymerase. The next question regarding this promising compound was whether it was effective against VZV in vivo.

In this study, we evaluated L-BHDU in a range of models that address cytotoxicity and efficacy in culture and in vivo. We have developed systems for screening potential antiviral compounds against VZV that employ fully differentiated, intact human tissues and live animals in an attempt to more closely mimic what occurs during a natural infection (Rowe et al.). The cytotoxic and antiviral effects of L-BHDU were first examined in a primary cell line, human foreskin fibroblasts (HFFs), and then ex vivo in a skin organ culture (SOC) model (Taylor and Moffat, 2005). Finally, the effects of L-BHDU were tested against VZV in SCID-Hu mice with human skin xenografts (Moffat and Arvin, 1999). This screening process employs the recombinant strain VZV-BAC-Luc, which was selected for its expression of firefly luciferase that can be quantitatively measured by bioluminescence, as well as for its wild type virulence and tissue tropism (Zhang et al., 2007). We report that L-BHDU prevented VZV replication in HFFs as wells as in skin explants and xenografts in the SCID-Hu mouse. This demonstrates the potential of L-BHDU as a novel anti-VZV agent.

OBJECTS OF THE INVENTION

It is an object of the present invention to provide compounds, pharmaceutical compositions and methods of treating and/or preventing infections from Varicella-Zoster virus (VZV) and related conditions and/or disease states (especially including Shingles) and post-herpetic neuralgia in patients in need.

BRIEF DESCRIPTIONS OF THE FIGURES

FIG. 1 shows cytotoxicity and reversibility assays. (A) A neutral red dye uptake assay was performed using HFFs. Cells were treated with either L-BHDU from 0.1-200 μM or DMSO diluent equal to the concentration in 200 μM L-BHDU. Staurosporine (35 nM) induces apoptosis and served as a positive control for cell death. Each point represents the mean standard deviation of six replicate samples. (B) The reversibility of L-BHDU antiviral activity was determined. HFFs were infected with VZV-BAC-Luc and treated with DMSO diluent (squares) or 2 μM L-BHDU for 0-24 h (open circles) or 0-72 h (closed circles). VZV spread was determined by daily bioluminescence imaging of the same cultures. Background from uninfected and untreated HFFs was $1.4 \times 10^6$ total flux (photons/s). Each point represents the mean±standard deviation of triplicate samples. These results for (A) and (B) are representative of three separate experiments.

Figure 2:
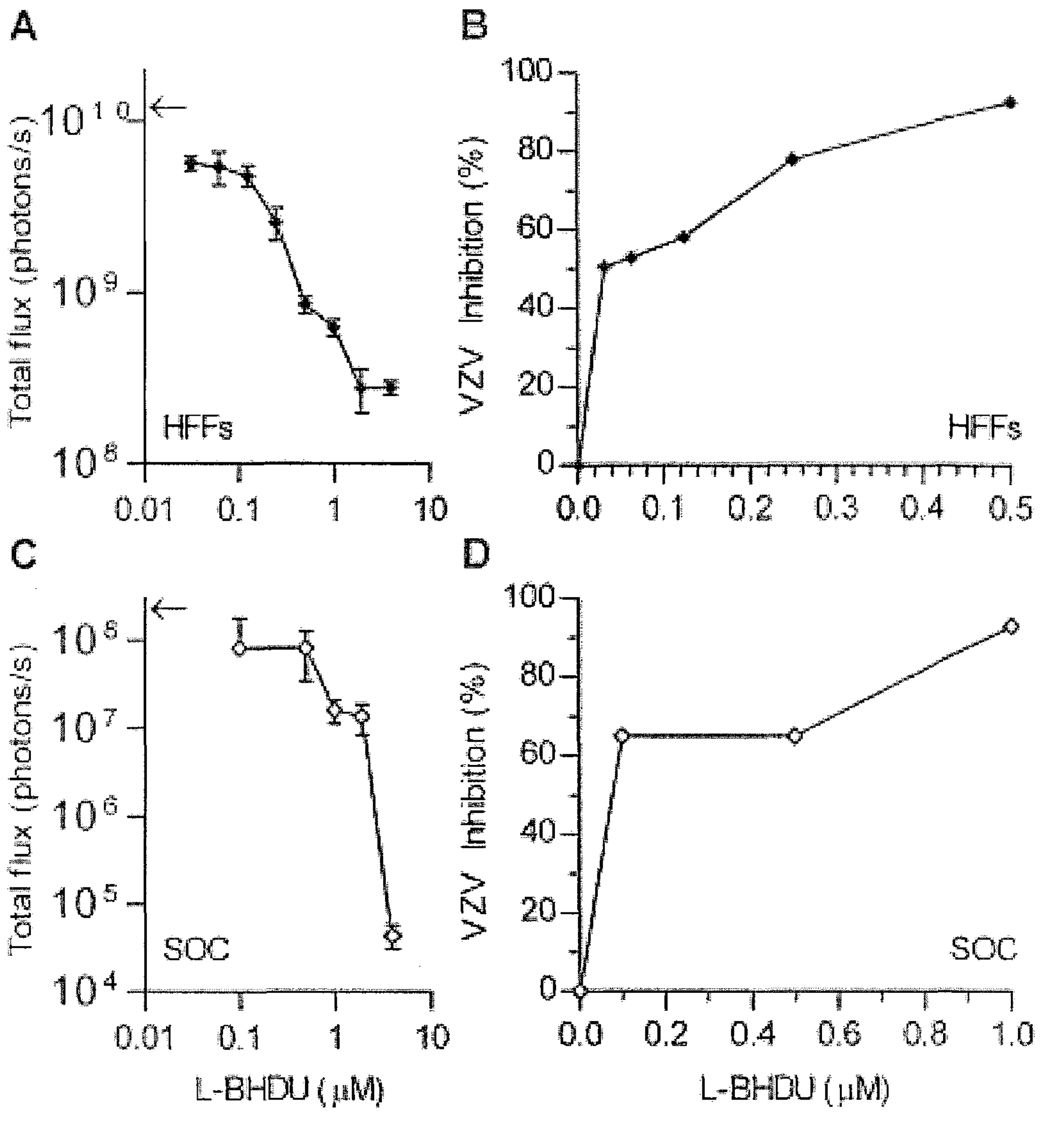

FIG. 2 shows $EC_{50}$ determination in HFFs and SOC. (A) HFFs were infected with VZV-BAC-Luc and treated for 48 h with 2-fold dilutions of L-BHDU ranging from 0.03-4.0 μM, or with the amount of DMSO diluent in the highest drug concentration. VZV yield was determined via daily bioluminescence imaging of the same cultures. Each point represents the mean±standard deviation of triplicate samples. (B) The percentage of virus growth inhibition was calculated from the values in (A) and the $EC_{50}$ in culture was interpolated as 0.03 μM. (C) Skin explants were infected with VZV-BAC-Luc and treated for 6 days with L-BHDU ranging from 0.1-4.0 μM. (D) VZV yield in skin explants was measured at 6 dpi and the percentage of virus inhibition was calculated and used to estimate the $EC_{50}$ as <0.1 μM. Arrows in (A) and (C) indicate VZV yield in cultures treated with diluent. Each point represents the mean±standard deviation of triplicate samples. These results are representative of two separate experiments.

Figure 3:
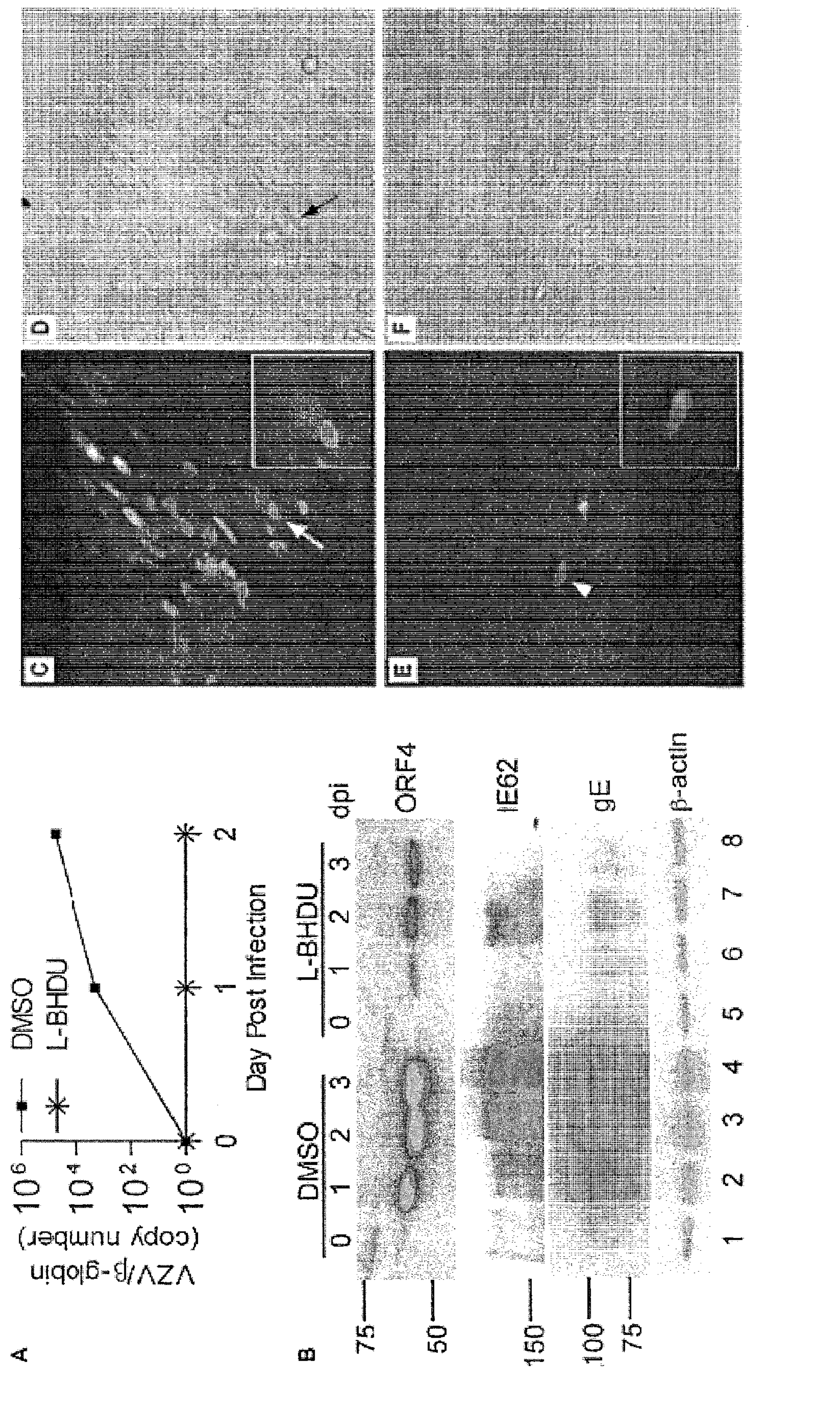

FIG. 3 shows the effects of L-BHDU on VZV DNA and protein synthesis. (A) VZV genome copy number was determined by quantitative real-time PCR. HFFs were infected with VZV-BAC-Luc and treated with 2 μM L-BHDU or diluent, and then DNA was extracted and analyzed for VZV ORF38 and human β-globin. The gene copy number of ORF38 was normalized to β-globin in each sample. These results are representative of two separate experiments. (B) Immunoblots for VZV ORF4 protein, IE62 protein, and glycoprotein E (gE) were performed on cell lysates obtained from aliquots of the same samples used for qPCR in (A). The autoradiographs were overexposed to reveal small amounts of VZV proteins in cultures treated with 2 μM L-BHDU (lanes 5-8). β-actin was a loading control. (C-F) HFFs were grown on chamber slides and infected with VZV-IE62-mRFP. Cultures were treated with DMSO diluent alone (C, D) or 2 μM L-BHDU (E, F) for 48 h. IE62-mRFP localization was detected by fluorescence microscopy (C, E). Phase contrast images of the cell monolayers show CPE (D, arrow). Magnification, ×40.

Figure 4:
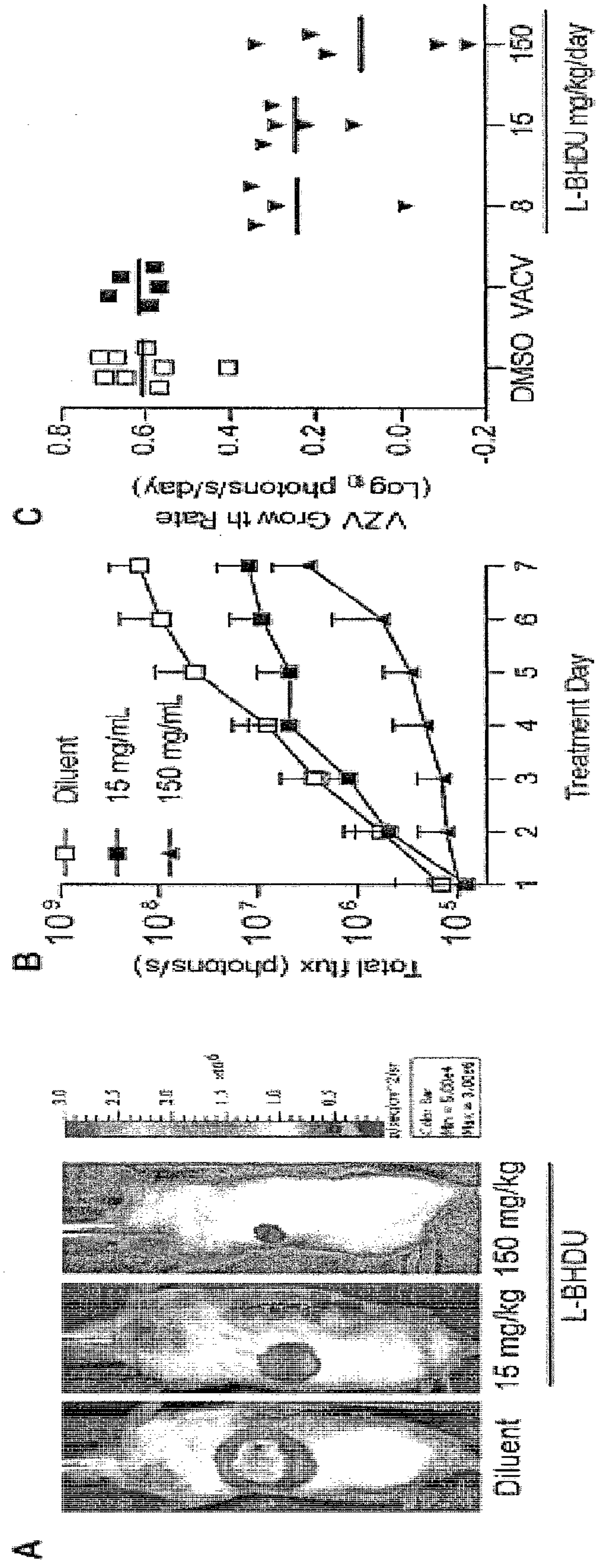

FIG. 4 shows the evaluation of L-BHDU in vivo. (A) Bioluminescence images of representative mice from three treatment groups are shown at 5 dpi. A pseudocolored depiction of light emissions (photons/s/$cm^2$/steradian) was overlaid on a photograph of the mice. The scale bar indicates the colors assigned to the signal intensity values from $5 \times 10^4$ (purple) to $3 \times 10^6$ (red). Photons were detected directly above the skin implants on the left flank. (B) The average total flux values for the groups shown in (A) were plotted versus the treatment day. Each point represents the mean±standard deviation of the group. (C) The VZV growth rate for individual mice (symbols) and the average for the group (bars) are shown. All doses of L-BHDU (triangles) caused significant reduction compared to the diluent group (open squares) using the Mann-Whitney U two-tailed test. For details see Table 1, FIG. 5. Data from 2 separate experiments are shown.

FIG. 5, Table 1 shows the differences in VZV growth rates between diluent (DMSO control), validiclovir, and various concentrations of L-BHDU. Combined data from two separate experiments demonstrate that the DMSO diluent (n=8) had no effect on the VZV growth rate, producing a rate of 0.61±0.10 $\log_{10}$ photons/s/day that exceeded the typical results in cultured HFFs of 0.50 (½ $\log_{10}$ per day). The average rate of VZV growth in the mice treated with valaciclovir (n=5) was 0.62±0.05 $\log_{10}$ photons/s/day, which is nearly identical to that of the diluent treated group, thus there was no antiviral effect. The low doses of L-BHDU (8 and 15 mg/kg/day) caused an intermediate reduction in the VZV growth rate at 0.24-0.25 $\log_{10}$ photons/s/day, and the high dose (150 mg/kg/day) almost completely prevented VZV replication and reduced the growth rate to 0.09±0.21 $\log_{10}$ photons/s/day. The differences in VZV growth rates between all doses of L-BHDU and the diluent were significant. No overt toxicity from L-BHDU was seen in vivo. L-BHDU and DMSO both caused moderate weight loss, which did not correspond to dose, and mortality was ⅛ in the DMSO group and ⅕ in the 8 mg/kg/day L-BHDU group. The valaciclovir group lost >20% of body weight, suggesting mice were averse to the drug in water.

FIG. 6, Table 2 shows the concentrations of L-BHDU in mouse organs and the human skin xenografts. Tissue and plasma specimens were collected two hours after the final treatment, and then drug concentrations were measured by HPLC. The maximum concentration ($C_{max}$, μg/mL of plasma or μg/g of tissue) was determined and the ratio to plasma was calculated and presented. The results of Table 2 are discussed in greater detail in the examples section.

BRIEF DESCRIPTION OF THE INVENTION

The present invention relates to compounds according to the general formula I:

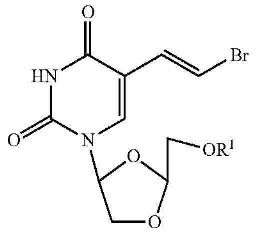

1

Where $R^1$ is H, an amino acyl group derived from an amino acid (preferably, a L- or D-amino acid, preferably an L- or D-alpha amino acid), preferably an L-α-amino acid (preferably, an amino acyl group derived from valine, phenylalanine, leucine, isoleucine, threonine, alanine or glycine) or a phosphoamidate group according to the chemical structure:

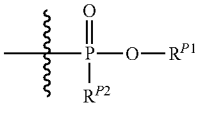

Where $R^{P1}$ is a $C_1$-$C_{20}$ linear, branched or cyclic alkyl group, or an optionally substituted aryl, heteroaryl or heterocyclic group; and $R^{P2}$ is a —$NR^{N1}R^{N2}$ group or a B' group;

Where $R^{N1}$ and $R^{N2}$ are each independently H or a $C_1$-$C_{20}$ alkyl group, preferably a $C_1$-$C_6$ alkyl group which is optionally substituted with one, two or three hydroxyl groups, an optionally substituted phenyl group (e.g., benzyl), heteroaryl or heterocyclic group (preferably $R^{N1}$ is H); and B' is a

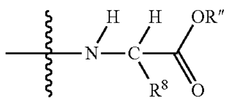

group;

Where $R^8$ is sidechain of an amino acid, preferably a sidechain of an amino acid (as otherwise described herein) preferably selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine (preferably $R^8$ is derived from alanine, leucine, valine, isoleucine or threonine), and R" is a $C_1$ to $C_{20}$ linear, branched or cyclic alkyl group, an aryl group, heteroaryl group or heterocyclic group, each of which groups is optionally substituted, or a pharmaceutically acceptable salt, anomer, solvate or polymorph thereof.

Preferred compounds according to the present invention include those wherein $R^1$ is an acyl amino group derived from an amino acid, preferably an L-α amino acid, even more preferably an L-α amino acid selected from the group consisting of valine, phenylalanine, leucine, isoleucine, alanine or glycine. Preferably, $R^1$ is an amino acid group derived from valine, leucine, isoleucine or glycine, even more preferably valine. It is an unexpected result that compounds according to the present invention exhibit anti-VZV activity at levels which are as much as 10-100 fold greater than prior art compound and consequently, provide an unexpectedly enhanced therapeutic index in the treatment of VZV in patients relative to prior art compounds. Compounds according to the present invention exhibit greater anti-VZV activity in many instances and reduced toxicity, such that the therapeutic index of the composition may be enhanced along with enhanced anti-VZV therapy as well. Treatment of secondary conditions such as rash, as well as recurrent infection (shingles) is noted with the present compounds. In addition, compounds according to the present invention may be used to treat drug resistant VZV infections, especially VZV infections which have been become resistant to one or more of the agents currently used to treat VZV infections, including acyclovir and its derivatives, including valaciclovir (VACV), penciclovir (PCV) and famciclovir (FCV), phosphonoformate, and idoxuridine, trifluridine and brivudin.

In another aspect of the invention, pharmaceutical compositions according to the present invention comprise an effective amount of at least one compound as otherwise described herein, optionally in combination with a pharmaceutically acceptable carrier, additive or excipient, further optionally in combination with another anti-VZV agent. Preferred compounds for use in the pharmaceutical aspect of the invention include those where $R^1$ is an acyl amino group derived from an amino acid, preferably an L-α amino acid, even more preferably an L-α amino acid selected from the group consisting of valine, phenylalanine, leucine, isoleucine, alanine or glycine. It has unexpectedly been discovered that when $R^1$ is an amino acid group derived from valine, leucine, isoleucine or glycine, even more preferably valine, that such compounds when used in treating VZV infections. It is an unexpected result that compounds according to the present invention exhibit anti-VZV activity at levels which are as much as 10-100 fold greater than prior art compound and consequently, provide an unexpectedly enhanced therapeutic index in the treatment of VZV in patients relative to prior art compounds.

In another aspect, the present invention relates to a method of treating a VZV infection, including a secondary disease state or condition of VZV (including a rash, post-herpetic neuralgia or recurrent VZV or shingles), the method comprising administering to a patient in need an effective amount of at least one compound according to the present invention as described above in combination with a pharmaceutically acceptable carrier, additive or excipient, optionally in combination with another anti-VZV agent selected from the group consisting of acyclovir (ACV), valaciclovir (VACV), penciclovir (PCV) and famciclovir (FCV), phosphonoformate, idoxuridine, trifluridine and brivudin.

In yet another aspect, the present invention relates to a method for reducing the likelihood of a recurrent VZV infection (Shingles) and/or post-herpetic neuralgia comprising administering to a patient at risk of Shingles with an effective amount of at least one compound according to the present invention as described above in combination with a pharmaceutically acceptable carrier, additive or excipient, optionally in combination with another anti-VZV agent.

DETAILED DESCRIPTION OF THE INVENTION

The following terms are used to describe the present invention. In instances where a term is not specifically defined herein, that term is given an art-recognized meaning by those of ordinary skill applying that term in context to its use in describing the present invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The term "compound", as used herein, unless otherwise indicated, refers to any specific chemical compound disclosed herein, generally refers to 13-L nucleoside analogs, but may include, within context, tautomers, regioisomers, geometric isomers, including anomers, and where applicable, optical isomers (enantiomers) thereof, as well as pharmaceutically acceptable salts thereof, solvates and/or polymorphs. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds.

The term "patient" or "subject" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal. In general, in the present invention, the term patient refers to a human patient unless otherwise stated or implied from the context of the use of the term.

The term "Varicella Zoster Virus" or "VZV" is used to describe Herpesvirus varicellae, also known as chicken pox or herpes zoster (shingles). VZV is a herpes virus and is morphologically identical to Herpes Simplex virus, that causes varicella (chicken pox), and herpes zoster (recurrent chicken pox or shingles) in humans. Varicella result from a primary infection with the virus; herpes zoster (shingles) results from secondary invasion by the same or by reactivation of infection which in many instances may have been latent for a number of years.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, amide, phosphoamidate or other prodrug group) which, upon administration to a patient, provides directly or indirectly the present compound or an active metabolite of the present compound.

The term "independently" is used herein to indicate that the variable, which is independently applied, varies independently from application to application.

The term "alkyl" shall mean within its context a linear, branch-chained or cyclic fully saturated hydrocarbon radical or alkyl group, preferably a $C_1$-$C_{20}$, more preferably a $C_1$-$C_{10}$, alternatively a $C_8$-$C_{20}$ alkyl group, which may be optionally substituted.

The term "unsubstituted" shall mean substituted only with hydrogen atoms. The term "substituted" shall mean, within the chemical context of the compound defined, a substituent (each of which substituents may itself be substituted) selected from a hydrocarbyl (which may be substituted itself, preferably with an optionally substituted alkyl or fluoro group, among others), preferably an alkyl, more preferably a $C_1$-$C_6$ alkyl (preferably a $C_1$-$C_3$ alkyl), including $CF_3$, halogen (F, Cl, Br, I), thiol, hydroxyl, carboxyl, C alkoxy, $C_1$-$C_6$ oxycarbonyl ester, $C_1$-$C_6$ carbonyloxy ester, CN, nitro or an optionally substituted amine (e.g. an alkyleneamine or a $C_1$-$C_6$ monoalkyl or dialkyl amine). Various optionally substituted moieties may be substituted with 3 or more substituents, preferably no more than 3 substituents and preferably with 1 or 2 substituents. It is noted that in instances where a compound is substituted at a particular position of a molecule, but no substitution is indicated, although the valence of the molecule requires substitution, then that substituent is H.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" refers to a cyclic group which contains at least one heteroatom, i.e., O, N or S, and may be aromatic (heteroaryl) or non-aromatic. Exemplary heteroaryl groups are described hereinabove. Exemplary non-aromatic heterocyclic groups for use in the present invention include, for example, pyrrolidinyl, pyrrolinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide and succinimide, among others.

The term "amino acid" or "amino acid residue" shall mean, within context, a radical of a D- or L-amino acid (preferably an L-α-amino acid) which is covalently bound to a nucleoside analog at the 5'-OH position of the sugar synthon (e.g., R') through a carboxylic acid moiety of the amino acid, thus forming respectively, an ester group (referred to as an "amino acyl" group) linking the nucleoside to the amino acid, or forming a phosphoramidate group (as B') as otherwise described herein. Representative amino acids include both natural and unnatural amino acids, preferably including, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others. Preferred amino acids for use in the present invention (especially substituted at R') include valine, phenylalanine, leucine, isoleucine, threonine, alanine or glycine, more preferably valine, isoleucine, leucine and threonine, even more preferably valine (especially as a substituent on $R^1$).

The term "phosphoamidate" is used throughout the specification to describe a group which is found at the 5' position of the sugar synthon of the nucleoside compound and froms a prodrug form of the nucleoside analog. Phosphamidate groups for use in the present invention include those represented by the structure:

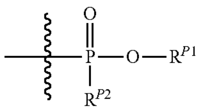

Where $R^{P1}$ is a $C_1$-$C_{20}$ linear, branched or cyclic alkyl group, or an optionally substituted aryl, heteroaryl or heterocyclic group; and $R^{P2}$ is a —$NR^{N1}R^{N2}$ group or a B' group;

Where $R^{N1}$ and $R^{N2}$ are each independently H or a $C_1$-$C_{20}$ alkyl group, preferably a $C_1$-$C_6$ alkyl group which may be optionally substituted with one, two or three hydroxyl groups, and B' is a

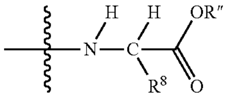

group;

Where $R^8$ is sidechain of an amino acid, preferably a sidechain of an amino acid (as otherwise described herein) preferably selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine (preferably $R^8$ is derived from alanine, leucine, valine, isoleucine or threonine), and R" is an optionally substituted $C_1$ to $C_{20}$ linear, branched or cyclic alkyl group or an optionally substituted aryl, heteroaryl or heterocyclic group as otherwise described herein.

Preferred $R^{P1}$ groups include optionally substituted $C_8$-$C_{20}$ alkyl groups and optionally substituted phenyl, naphthyl and monocyclic heteroaryl groups, especially those groups (particularly lipophilic groups) which enhance bioavailability of the compounds in the skin of the patient and which exhibit reduced toxicity, enhanced therapeutic index and enhanced pharmacokinetics (the compounds are metabolized and excreted more slowly).

The term "effective amount" shall mean an amount or concentration of a compound according to the present invention which is effective within the context of its administration, which may be inhibitory, prophylactic and/or therapeutic. Within context, all active compounds which are used in the present invention are used in effective amounts. The present compound also relates to combinations of compounds which contain effective amounts of each of the compounds used, whether that combination is additive or synergistic in effect, provided that the overall effect of the combination of compounds is to inhibit, reduce and/or treat VZV infections, especially including recurrent VZV infections or shingles. Effective therapy may be measured by measuring VZV concentrations (titers) in a patient, including a patient suspected of being at risk for shingles but who exhibits no active symptomology associated with a VZV infection.

The term "L-configuration" as used in the context of the present invention refers to the configuration of the nucleoside compounds according to the present invention which mimics the unnatural configuration of sugar moieties as opposed to the natural occurring nucleosides or "D" configuration. The term "β" or "β anomer" is used to describe nucleoside analogs according to the present invention in which the nucleoside base (in this case pyrimidine) is configured (disposed) above the plane of the carbocyclic moiety in the nucleoside analog.

The term "enantiomerically enriched" is used throughout the specification to describe a nucleoside which includes at least about 95%, preferably at least about 96%, more preferably at least about 97%, even more preferably, at least about 98%, and even more preferably at least about 100% or more of a single enantiomer of that nucleoside. The purine nucleoside compounds according to the present invention are generally β-L-nucleoside analog compounds. When the present compounds according to the present invention are referred to in this specification, it is presumed that the nucleosides have the L-nucleoside configuration and are enantiomerically enriched (preferably, about 100% of the L-nucleoside), unless otherwise stated or construed otherwise within the context of a description of the present invention.

The terms "coadminister" and "coadministration" are used synonymously to describe the administration of at least one of the nucleoside compounds according to the present invention in combination with at least one other agent, preferably at least one additional anti-VZV agent (as otherwise described herein), including other nucleoside anti-VZV agents which are specifically disclosed herein in amounts or at concentrations which would be considered to be effective amounts at or about the same time. While it is preferred that coadministered agents be administered at the same time, agents may be administered at times such that effective concentrations of both (or more) agents appear in the patient at the same time for at least a brief period of time. Alternatively, in certain aspects of the present invention, it may be possible to have each coadministered agent exhibit its inhibitory effect at different times in the patient, with the ultimate result being the inhibition of VZV, as well as the reduction or inhibition in VZV. Of course, when more than one viral or other infection or other condition is present, the present compounds may be combined with other agents to treat that other infection or condition as required.

The term "additional anti-VZV agent" shall mean a traditional anti-VZV agent (i.e., other than a compound according to the present invention) which may be co-administered to a patient along with at least one compound according to the present invention in treating a patient for VZV, including shingles. Such compounds include, for example, agents such as acyclovir and its derivatives, including valaciclovir (VACV), penciclovir (PCV), famciclovir (FCV), phosphonoformate, idoxuridine, trifluridine and brivudin, among others.

The terms "treat", "treating", and "treatment", etc., as used herein, refer to any action providing a benefit to a patient at risk for a VZV infection, especiall shingles or having a VZV infection, including improvement in the condition through lessening or suppression of titers of VZV, or at least one symptom of VZV, especially including VZV rashes, prevention or delay in progression of the disease, prevention or delay in the onset of disease states or conditions which occur secondary to VZV. Treatment, as used herein, encompasses both prophylactic and therapeutic treatment. The term "prophylactic" when used, means to reduce the likelihood of an occurrence or the severity of an occurrence within the context of the treatment of an infection of VZV, as otherwise described hereinabove.

Pharmaceutical compositions based upon the nucleoside compounds according to the present invention comprise one or more of the above-described compounds (which may or may not include an additional anti-VZV agent as otherwise described herein) in a therapeutically effective amount for inhibiting VZV, in particular in the treatment or prophylaxis of VZV or a VZV infection, including recurrence of a VZV infection (shingles), optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated.

In the pharmaceutical aspect according to the present invention, the compound according to the present invention is formulated preferably in admixture with a pharmaceutically acceptable carrier. In general, it is preferable to administer the pharmaceutical composition in orally-administrable form, but certain formulations may be administered via a parenteral, intravenous, intramuscular, transdermal, buccal, subcutaneous, suppository or other route, including intranasal spray. Intravenous and intramuscular formulations are preferably administered in sterile saline. In certain instances, transdermal administration may be preferred. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, the pro-drug form of the compounds, especially including acylated (acetylated or other) and ether (alkyl and related) derivatives, phosphate esters and various salt forms of the present compounds, are preferred. One of ordinary skill in the art will recognize how to readily modify the present compounds to pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, especially a VZV infection, reducing the likelihood of a VZV recurrence (shingles) or the inhibition, reduction and/or abolition of VZV. In general, a therapeutically effective amount of the present compound in pharmaceutical dosage form usually ranges from about 0.001 mg/kg to about 100 mg/kg per day or more, more preferably, slightly less than about 0.1 mg/kg to more than about 25 mg/kg per day of the patient or considerably more, depending upon the compound used, the condition or infection treated and the route of administration. The active nucleoside compound according to the present invention is preferably administered in amounts ranging from about 0.1 mg/kg to about 15 mg/kg per day of the patient, depending upon the pharmacokinetics of the agent in the patient. This dosage range generally produces effective blood level concentrations of active compound which may range from about 0.001 to about 100, about 0.05 to about 100 micrograms/cc of blood in the patient. For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral or intranasal administrations per day (for example, Q.I.D.) or transdermal administration and may include oral, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the bioavailability/pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

In particularly preferred embodiments according to the present invention, the compounds and compositions are used to treat, prevent or delay a VZV infection or the recurrence of a VZV infection (shngles) where VZV has become latent in a patient. It is believed that the compounds according to the present invention reduce, inhibit and/or eliminate latent VZV or the likelihood that latent VZV will cause a recurrence of a VZV infection.

Preferably, to treat, prevent or delay the onset of these infections and/or to reduce the likelihood of a recurrence of VZV, the compositions will be administered in oral dosage form in amounts ranging from about 250 micrograms up to about 500 mg or more at least once a day, preferably, up to four times a day. The present compounds are preferably administered orally, but may be administered parenterally, topically or in suppository form, as well as intranasally, as a nasal spray or as otherwise described herein.

In the case of the co-administration of the present compounds in combination with another anti-VZV compound, the amount of the nucleoside compound according to the present invention to be administered ranges from about 0.01 mg/kg. of the patient to about 500 mg/kg. or more of the patient or considerably more, depending upon the second agent to be co-administered and its potency against VZV, the condition of the patient and severity of the disease or infection to be treated and the route of administration. The other anti-VZV agent may be preferably administered in amounts ranging from about 0.01 mg/kg to about 500 mg/kg. In certain preferred embodiments, these compounds may be preferably administered in an amount ranging from about 0.5 mg/kg to about 50 mg/kg or more (usually up to about 100 mg/kg), generally depending upon the pharmacokinetics of the two agents in the patient. These dosage ranges generally produce effective blood level concentrations of active compound in the patient.

The compounds according to the present invention, may advantageously be employed prophylactically to prevent or reduce the likelihood of a VZV infection, including a recurrence of VZV (shingles) or to prevent or reduce the likelihood of the occurrence of clinical symptoms associated with the viral infection or to prevent or reduce the likelihood of the spread of a viral infection to another person. Thus, the present invention also encompasses methods for the prophylactic treatment of VZV and in particular, the reduction in the likelihood of a recurrence of VZV (shingles) in an individual who has previously had a VZV infection at an earlier time. In this aspect according to the present invention, the present compositions are used to prevent, reduce the likelihood of or delay the onset of a viral infection or a virus related disease or condition or the spread of infection to other people. This prophylactic method comprises administering to a patient in need of such treatment or who is at risk for the development of a VZV infection and in particular, a recurrence of a VZV infection where the infection has become latent, an amount of a compound according to the present invention alone or in combination with another anti-VZV agent effective for alleviating, preventing or delaying the onset of the viral infection. In the prophylactic treatment according to the present invention, it is preferred that the antiviral (anti-VZV) compound utilized should be as low in toxicity and preferably non-toxic to the patient. It is particularly preferred in this aspect of the present invention that the compound which is used should be maximally effective against the virus and should exhibit a minimum of toxicity to the patient. In the case of compounds of the present invention for the prophylactic treatment of viral infections, these compounds may be administered within the same dosage range for therapeutic treatment (i.e., about 250 micrograms up to about 500 mg. or more from one to four times per day for an oral dosage form) as a prophylactic agent to prevent the proliferation of the viral infection or alternatively, to prolong the onset of or reduce the likelihood of a patient contracting a virus infection which manifests itself in clinical symptoms. It is noted that the present compounds have a high or large therapeutic index (high activity/low toxicity) compared to prior art compounds, making them particularly use for the reduction in the likelihood of a recurrence of VZV (shingles).

In addition, compounds according to the present invention may be administered alone or in combination with other agents, including other compounds of the present invention. Certain compounds according to the present invention may be effective for enhancing the biological activity of certain agents according to the present invention by reducing the metabolism, catabolism or inactivation of other compounds and as such, are co-administered for this intended effect.

The present invention is now described, purely by way of illustration, in the following examples. It will be understood by one of ordinary skill in the art that these examples are in no way limiting and that variations of detail can be made without departing from the spirit and scope of the present invention.

EXAMPLES

The α-herpesvirus varicella-zoster virus (VZV) causes chickenpox and shingles. Current treatments are acyclovir, valaciclovir (VACV), famciclovir and brivudin. Vaccines are also approved that lower the incidence of primary and recurrent infections. Additional antiviral compounds with increased potency and specificity are needed to treat VZV and for strains resistant to the existing drugs. L-BHDU (MW 319.1) had anti-VZV activity in pilot studies. We evaluated L-BHDU in 3 models of VZV replication: primary human foreskin fibroblasts (HFFs), skin organ culture (SOC) and in SCID-Hu mice with skin xenografts. Virus replication was measured by bioluminescence imaging of the VZV-BAC-Luc strain. In HFFs, 100 μM L-BHDU was noncytotoxic over 3 days, and the antiviral effects of 2 μM treatment were reversible by XXX. L-BHDU treatment reduced VZV genome copy number, virus proteins levels, and cell to cell spread in HFFs. The $EC_{50}$ in HFFs was ~0.03 μM and in SOC was <0.1 μM. In mouse studies, L-BHDU in DMSO was administered by oral gavage once daily for 7 days, or 3 mg/mL VACV was added to drinking water, starting 2 dpi. Groups (n=5) were given 8, 15, or 150 mg/kg/day L-BHDU, and all doses significantly reduced VZV growth compared to VACV or DMSO. VACV was not effective and the group lost >20% of body weight, suggesting mice were averse to the drug in water. L-BHDU and DMSO caused moderate weight loss, which did not correspond to dose, and mortality was ⅛ in the DMSO group and ⅕ in the 8 mg/kg/day group. Mouse organs were harvested 2 h after the last dose. $C_{max}$ values for L-BHDU in the human skin xenografts were 0.7±0.1 μg/g and 11.3±1.1 μg/g for the 8 and 150 mg/kg/day doses, respectively. Comparison of concentration ratios of tissue to plasma indicated saturation of uptake at the higher dose. L-BHDU was effective and well tolerated in mice, therefore it has potential as a novel antiviral agent for VZV.

Varicella-zoster virus (VZV) is a human-restricted alphaherpesvirus. It causes varicella (chicken pox) upon primary infection and zoster (shingles) upon reactivation from latency. VZV disease is partially preventable by inoculation with the live, attenuated vaccine strain Oka-Merck (Oxman et al., 2005; Vazquez et al., 2004). Pediatric vaccination has reduced varicella cases in the United States (Seward et al., 2008), although the incidence of zoster is not likely to decline in the near future because in older adults the vaccine efficacy is approximately 50% (Holcomb and Weinberg, 2006). There will continue to be a demand for antiviral drugs for VZV due to natural and breakthrough cases and in immunocompromised patients that cannot receive live virus vaccines. Current treatments are nucleoside and pyrophosphate analogues that target the virus DNA polymerase and may depend on virus thymidine kinase activity (De Clercq, 2004). Acyclovir (ACV) and its derivatives valaciclovir (VACV), penciclovir (PCV) and famciclovir (FCV) are acyclic derivatives of guanine. They are moderately effective against VZV, but for best results treatment should begin within 72 h of rash onset and resistance may arise during long-term administration to immunocompromised patients (Sampathkumar et al., 2009). In these patients, Foscarnet (phosphonoformate) delivered intravenously may be necessary to treat resistant VZV (Ahmed et al., 2007). These drugs are widely approved for use in the United States, Europe, and Asia.

The cyclic derivatives of uridine are another class of drugs currently used to treat VZV. Infections in the eye (herpes zoster ophthalmicus) can be treated with topical idoxuridine and trifluridine. Brivudin [BVDU, (E)-5-(2-bromovinyl)-2'-deoxyuridine] is approved for use in Europe and was the first bromovinyl nucleoside analog to show anti-herpesvirus activity (De Clercq et al., 1979). BVDU is phosphorylated by the virus-encoded thymidine kinase (TK) to both the 5'-monophosphate and 5'-diphosphate forms. Cellular kinases produce the 5'-triphosphate form (BVDU-TP). BVDU-TP interacts with the viral DNA polymerase either as a competitive inhibitor or an alternative substrate whereby it can be incorporated into the DNA chain (reviewed in (De Clercq, 2005)). BVDU is more potent against VZV than acyclovir and its derivatives (Andrei et al., 1995; Shigeta et al., 1983). Another benefit of BVDU over acyclovir is the ease of dosing, making it appealing to elderly patients (De Clercq, 2005). The main drawback of BVDU is that it is cleaved into a metabolite of BVU. BVU in turn inhibits dihydropyrimidine dehydrogenase, which is involved in the degradation of thymidine, uracil, and the commonly used cancer drug 5'-fluorouracil (5-FU). Patients receiving this chemotherapy regimen should not be given BVDU as it may cause toxic accumulation of 5-FU and result in death [reviewed in (De Clercq, 2004; De Clercq, 2005; Diasio, 1998; Keizer et al., 1994)].

The serious possible adverse effects of BVDU are the main reason why related compounds have been screened for antiviral activity without the potential toxicity. One approach has been to screen nucleosides in the non-naturally occurring L-configuration, which can be just as effective as the D-nucleoside counterparts (Chu et al., 1995; Spadari et al., 1992). The uridine derivative, β-L-1-[5-(E-2-Bromovinyl)-2-(hydroxymethyl)-1,3-dioxolan-4-yl)]uracil (L-BHDU), exhibited potent anti-VZV activity in cultured cells and it was noncytotoxic in HEL 299 cells up to 200 μM (Choi et al., 2000; Li et al., 2000). Efforts to elucidate the mechanism of action found that L-BHDU was phosphorylated by VZV TK but not further converted to the di- and triphosphate forms. This is different from BVDU and implies an alternative antiviral mechanism (Li et al., 2000). Their evidence pointed to the monophosphate form as the active moiety that would inhibit VZV DNA polymerase. The next question regarding this promising compound was whether it was effective against VZV in vivo.

In the present study, the inventors evaluated L-BHDU in a range of models that address cytotoxicity and efficacy in culture and in vivo. We have developed systems for screening potential antiviral compounds against VZV that employ fully differentiated, intact human tissues and live animals in an attempt to more closely mimic what occurs during a natural infection (Rowe et al.). The cytotoxic and antiviral effects of L-BHDU were first examined in a primary cell line, human foreskin fibroblasts (HFFs), and then ex vivo in a skin organ culture (SOC) model (Taylor and Moffat, 2005). Finally, the effects of L-BHDU were tested against VZV in SCID-Hu mice with human skin xenografts (Moffat and Arvin, 1999). This screening process employs the recombinant strain VZV-BAC-Luc, which was selected for its expression of firefly luciferase that can be quantitatively measured by bioluminescence, as well as for its wild type virulence and tissue tropism (Zhang et al., 2007). We report that L-BHDU prevented VZV replication in HFFs as wells as in skin explants and xenografts in the SCID-Hu mouse. This demonstrates the potential of L-BHDU as a novel anti-VZV agent.

Materials and Methods

Propagation of Cells and Virus.

Human foreskin fibroblasts (HFFs) (CCD-1137Sk; American Type Culture Collection, Manassas, Va.), used prior to passage 20, were grown in Eagle minimum essential medium with Earle's salts and L-glutamine (HyClone Laboratories, Logan, Utah), supplemented with 10% heat-inactivated fetal bovine serum (Benchmark FBS; Gemini Bio Products, West Sacramento, Calif.), penicillin-streptomycin (5,000 IU/ml), amphotericin B (250 μg/ml), and nonessential amino acids (all Mediatech, Herndon, Va.). VZV-BAC-Luc (Zhang et al., 2007) was derived from the Parental Oka strain, a wild type clinical isolate from Japan (Accession number: AB097933). Dr. Hua Zhu (University of Medicine and Dentistry of New Jersey) kindly provided a master stock of VZV-BAC-Luc (passage 10). VZV-BAC-Luc was stored at −80° C. and grown on HFFs for up to 10 passages. VZV-IE62-mRFP was kindly provided by Dr. Paul R. Kinchington (University of Pittsburgh).

Preparation of Drugs.

L-BHDU was synthesized as previously reported (Choi et al., 2000). A stock solution of L-BHDU was prepared in dimethyl sulfoxide (DMSO, cat. No. D2650; Sigma Aldrich, St. Louis, Mo.), aliquoted, and stored at −20° C. until use. Valaciclovir HCl (VACV, 500 mg tablet, GlaxoSmithKline, RTP, NC) was crushed in a mortar and dissolved in water). Final drug dilutions used in all experiments were prepared fresh as indicated.

Prodrugs according to the present invention which contain a 5'-amino acyl group are synthesized by condensing an amino acid group onto the 5'-position of L-BHDU using the carboxylic acid group to form an ester with the 5'OH group of L-BHDU. Numerous appoaches well known in the art may be taken to provide 5'-O-amino acid prodrug compounds according to the present invention. The reaction is facile and proceeds in high yield.

Prodrug compounds which contain phosphoamidate groups at the 5' position of the sugar synthon of L-BHDU can be readily obtained stepwise from $POCl_3$ (phosphorous oxychloride) by first reacting an appropriately substituted alcohol which forms an $R^{P1}$ group with $POCl_3$ in the presence of an acid scavenger such as pyridine or triethylamine to form a monosubstituted dichlorooxyphosphorous compound. The monosubstituted dichlorooxyphosphorous compound obtained from the first step is then further reacted with a substituted amine to form a disubstituted chlorooxyphosphorous compound which has a RPI as an ether and a $R^{P2}$ group as an amine. The disubstituted chlorooxyphosphorous compound is then reacted with L-BHDU (in the presence of triethylamine) to form the 5'-phosphoramidate nucleoside compound as prodrug form of L-BHDU in high yield. Various combinations of this chemical synthesis may be provided for literally hundreds of prodrug forms used in the present invention.

Cytotoxicity Assay.

The neutral red (NR) cytotoxicity assay was performed as described previously (Rowe et al.) and is based on the method of (Babich et al., 2002).

Dose-Response Studies.

HFFs were seeded in 6-well plates 24 h prior to infection. HFFs were infected with cell-associated VZV-BAC-Luc showing more than 80% cytopathic effect (CPE) at either a 1:50 or 1:100 ratio of infected to uninfected cells and adsorbed for two hours at 37° C. Excess virus was removed and the cells were washed once with PBS. Cells were treated with DMSO diluent or increasing doses of L-BHDU (0.03-4.0 μM) for 72 h. Drugs were refreshed every 24 h. VZV yield was determined daily by bioluminescence imaging (see below) using the IVIS50™ instrument (Caliper Life Sciences/Xenogen, Hopkinton, Mass.). For recovery studies, 2 μM L-BHDU was used the same as above. Percentage of virus growth inhibition was calculated by dividing the total flux (photons/s) of L-BHDU at the indicated concentrations by the average total flux (photons/s) of DMSO diluent. This was converted into a percentage and subtracted from 100.

Quantitative PCR.

Quantitative PCR was performed as described previously (Taylor et al., 2004). The oligonucleotide primers and probe for human β-globin were 5'-CCTGATGCTGTTATGGGCAA-3' (forward), 5'-CCAGGCCATCACTAAAGGCA-3' (reverse), and FAM-5'-CTAAGGTGAAGGCTCATGGCAAGAAAGTGCT-3'-TAMRA (probe).

Immunoblotting.

Cells were harvested using sample buffer to extract proteins and blots were performed as in (Leisenfelder and Moffat, 2006). Approximately $1.7\times10^4$ cells per lane were separated on 10% SDS-polyacrylamide gel electrophoresis (SDS-PAGE) gels, transferred to PVDF membranes, and then probed with antibodies. Rabbit antisera to ORF4 or IE62 proteins was kindly provided by Dr. Paul R. Kinchington (University of Pittsburgh). $M_{ouse}$ monoclonal antibody to gE (3B3) was kindly provided by Dr. Charles Grose (University of Iowa). Mouse monoclonal antibody to f3-actin (A5441) was purchased from Sigma Aldrich (St. Louis, Mo.). Alkaline-phosphatase conjugated anti-rabbit and anti-mouse antibodies were purchased from Jackson ImmunoResearch (West Grove, Pa.). Detection was by enhanced chemiluminescence using the LumiPhos reagent (Pierce Biotechnology, Thermo Fisher Scientific, Inc., Rockford, Ill.).

Fluorescence Microscopy.

HFFs were grown to confluence on chamber slides and infected with a cell-associated inoculum of VZV-IE62-mRFP in the same manner as VZV-BAC-Luc. Infected cells were treated with DMSO diluent alone or 2 μM L-BHDU for 48 h, which was refreshed daily. Cells were viewed on an Olympus IX51 inverted fluorescent microscope with an Optronics Quantafire monochrome camera at 40× magnification.

Skin Organ Culture.

Human fetal skin tissue (13 to 24 weeks gestational age, Advanced Bioscience Resources, Alameda, Calif.) was obtained in accordance with all local, state, and federal guidelines. Skin was divided into approximately 1-$cm^2$ pieces, cultured on NetWells (Corning, N.Y.), and inoculated with VZV-BAC-Luc as in (Rowe et al., Taylor and Moffat, 2005). Inoculation of each tissue was by scarification with a 27-gauge needle. For bioluminescence imaging, skin explants were submerged in D-luciferin (300 μg/mL in PBS) for 1 h before scanning in the IVIS50™.

Animal Procedures.

Human fetal skin xenografts were introduced subcutaneously into 12-15-week-old NOD.Cg-Prkdc Il2R$\gamma^{null}$ SCID mice (Taconic, Hudson, N.Y.) as full-thickness dermal grafts as described previously with the exception that single implants were used instead of bilateral implants (Moffat et al., 1995). Four to six weeks after implantation, implants were inoculated with cell-associated VZV-BAC-Luc, and virus growth was monitored using the IVIS-200™ apparatus for bioluminescence imaging as described below. Inoculation of implants was performed as in (Rowe et al.). L-BHDU and DMSO were administered by oral gavage daily for 6-7 days. Final drug dilutions were prepared fresh in DMSO from 10 mM or 100 mM stocks. Valaciclovir (VACV) was administered in the drinking water at a final concentration of 3 mg/mL and refreshed daily. Mice were weighed on Day 0 post infection and again upon termination of the experiment. The average body weight difference (ABWD) was calculated for each test group by subtracting the average final weight from the average initial weight. Two hours after final treatment, the mice were euthanized for immediate collection of blood and tissues, which were stored in liquid nitrogen. The protocol was reviewed and approved by the Committee for Humane Use of Animals at SUNY Upstate Medical University.

Bioluminescence Imaging.

Imaging was performed exactly as described in (Rowe et al.). Briefly, cell and skin cultures were scanned with the IVIS50™ instrument; mice were scanned with the IVIS200™ instrument (Caliper Life Sciences/Xenogen, Hopkinton, Mass.). Cell and skin images were acquired for 1 min; in vivo images were acquired for an initial exposure time of 5 minutes; if pixels were saturated, additional images with shorter exposure times were acquired. Background signals were determined from mock-treated, uninfected cultures or in vivo by placing a 1-$cm^2$ region of interest (ROI) on the head between the ears of mice with VZV-infected skin implants. The rate of VZV spread in the skin implants was calculated as the slope of a line with $y=\log_{10}$ photons/s, and x=day of treatment, where slope=VZV growth rate ($\log_{in}$ photons/s/day). The time interval was set as the day after treatment was initiated to the day it ended.

Statistical Analysis.

Data from experiments in HFFs and skin organ culture were analyzed using Student's t test (Microsoft Excel). Data from mouse experiments were analyzed by the nonparametric Mann-Whitney U test using GraphPad Prism 5.02 for Windows (GraphPad Software, San Diego, Calif., www.graphpad.com). Data were expressed as the mean±standard deviation.

Results

Cytotoxicity Assays

To determine the toxicity of L-BHDU in culture, a neutral red dye uptake assay was performed. The amount of dye absorbed is directly proportional to cell number and membrane integrity (Repetto et al., 2008). Primary human foreskin fibroblasts (HFFs) were treated with either 35 nM staurosporine to induce apoptosis, DMSO diluent alone, or 0.1 to 200 μM L-BHDU, refreshed daily. The uptake of neutral red dye was evaluated at 0, 24, 48, and 72 h post treatment. Absorbance values from 6 replicates at each dose were averaged and plotted against treatment time (FIG. 1A). As expected, no viable cells were detected in the cultures treated with staurosporine. Dye uptake increased slightly or remained constant in cultures treated with DMSO or L-BHDU during the first 48 h, indicating that cells were viable and growing. In the cultures treated with 200 μM L-BHDU or DMSO at an equivalent diluent concentration, cell viability declined between 48-72 h. The results for all drug concentrations and the diluent overlapped extensively, indicating that any cytotoxic effects of L-BHDU were indistinguishable from those of DMSO. Even at 200 μM, a concentration far above the estimated $EC_{50}$ value (see section 3.2), L-BHDU was merely (Please use other word) cytostatic. This substantiates previous reports that L-BHDU caused no cell growth arrest up to 200 μM in HEL 299 cells (human embryonic lung) (Li et al., 2000).

Subtle cytotoxic effects of potential antiviral drugs may also be studied using a reversibility assay. If virus replication is reversible (replication continues after removal of the compound), then cell functions were not impaired and the compound is considered noncytotoxic. To evaluate the reversibility of L-BHDU, VZV-infected HFFs were treated with DMSO diluent or 2 μM L-BHDU for 24 or 72 h (treatment was refreshed every 24 h). VZV spread was measured by daily bioluminescence imaging of the same cultures. VZV grew normally in cultures treated with DMSO alone, increasing for the first 48 h and then reaching a maximum at 72 h as the HFFs were consumed by infection (FIG. 1B). In cultures treated continuously with 2 μM L-BHDU, the bioluminescence signal gradually declined, an indication that VZV spread was prevented and luciferase synthesis decreased. When the drug was removed from replicate cultures after 24 h, virus spread resumed at a rate of approximately ½ $\log_{10}$ per day, which is typical for VZV. Thus the antiviral effects of L-BHDU were reversible. Moreover, these results demonstrated that VZV-BAC-Luc was sensitive to L-BHDU at concentrations at least 100-fold lower than the highest tolerated dose for HFFs, and so further evaluation was merited.

$EC_{50}$ Determination in Cultured Cells and SOC

Two culture systems were employed to determine the L-BHDU $EC_{50}$: HFFs and SOC. Subconfluent HFFs were infected with a cell-associated inoculum of VZV-BAC-Luc for 2 h. Excess inoculum was then removed and medium containing either DMSO diluent or 2-fold dilutions of L-BHDU at concentrations between 0.03 and 4.0 μM were added; this point was deemed time zero. Cells were treated for 3 days, with drug containing medium refreshed daily. VZV spread was measured by daily bioluminescence imaging of the same cultures. VZV growth kinetics were typical in cultures treated with DMSO alone (data not shown, results were similar to FIG. 1B), whereas L-BHDU treatment caused a dose-dependent decrease in VZV yield (FIG. 2A). Increased variability in virus yield was observed at the lower drug concentrations, an indication that VZV was partially inhibited. The results from 2 dpi were selected for calculating the effective dose with 50% reduction in VZV titer ($EC_{50}$) since virus replication in the culture wells was unrestricted at this density. The percentage of virus growth inhibition at 2 dpi was calculated and plotted against L-BHDU concentration in order to interpolate the $EC_{50}$ (FIG. 2B), which was 0.03 μM in HFFs. This result was similar to the previously reported $EC_{50}$ values of 0.055 and 0.07 μM in HEL cells using the VZV Ellen strain (Choi et al., 2000; Li et al., 2000).

L-BHDU was next evaluated in skin where VZV infects epidermal keratinocytes and dermal fibroblasts (Cohen et al., 2007; Sexton et al., 1992). We used a skin organ culture (SOC) model that provides the differentiated cell types and the tissue microenvironment that is highly suitable for VZV replication (Taylor and Moffat, 2005). SOC also provides the relevant conditions for evaluating potential antiviral compounds against VZV (Rowe et al.). The L-BHDU dose-response in SOC was determined by infecting 1-$cm^2$ pieces of skin with VZV-BAC-Luc via scarification, and then triplicate skin samples were treated for 6 days with 0.1, 0.5, 1.0, 2.0, or 4.0 μM L-BHDU. Drug was refreshed every 24 h. The level of VZV infection was measured daily by bioluminescence imaging and reported as total flux (photons/s). Previous studies showed that skin explants retained their integrity for at least 10 days and VZV replication was unrestricted (Taylor and Moffat, 2005). Similar to the results in cultured HFFs, a dose-dependent antiviral effect of L-BHDU was observed in SOC (FIG. 2C). The effective dose with 50% reduction in VZV titer ($EC_{50}$) for skin was interpolated from results on Day 6 as <0.1 μM, which was the lowest dose tested. Although histopathological studies were not performed, neither DMSO nor L-BHDU treatment caused obvious detrimental effects to the tissue. Based on the maximal reduction in VZV spread observed in the skin explants at 4 μM (FIG. 2C), this concentration was selected as the lower limit for subsequent evaluations in mice (see section 3.4).

Effects of L-BHDU on VZV DNA Synthesis and Protein Expression

VZV TK phosphorylates L-BHDU and the monophosphate form is thought to inhibit the function of viral DNA polymerase (Li et al., 2000). This mode of inhibition is unlike other nucleoside analogues, which are active in the triphosphate forms, and so we investigated the effects of L-BHDU on viral DNA synthesis in infected cells using quantitative real-time PCR. DNA was isolated from infected cells treated with either DMSO diluent alone or 2 μM L-BHDU at 0-2 dpi and then the number of copies of VZV ORF38 DNA and human β-globin gene in the same samples were determined by quantitative, real time PCR. The copy number of ORF38 was then normalized to β-globin. The number of VZV genomes increased exponentially in the diluent control but remained below the level of detection in the cultures treated with L-BHDU. This was consistent with inhibition of DNA synthesis as the putative antiviral mechanism of L-BHDU.

Although L-BHDU prevented de novo viral DNA synthesis in treated cells, a large number of VZV genomes were present that could engage in viral mRNA and protein synthesis. In these antiviral assays, VZV infection was initiated with a cell-associated inoculum that contained abundant viral DNA, mRNA, and protein that might extend virus replication even in the presence of a DNA polymerase inhibitor such as L-BHDU. To investigate the effects of L-BHDU on VZV protein levels, infected cells were treated with either DMSO diluent alone or 2 μM L-BHDU, and then replicate cultures were harvested at days 0-3 dpi and subjected to immunoblot. Several proteins were evaluated that represent the major kinetic classes of VZV replication: immediate early ORF4 protein, the major immediate early transactivator ORF62/71 protein (IE62) that is also expressed in the early phase, and late glycoprotein E (gE). β-actin protein served as a loading control. As expected, these viral proteins accumulated in cells treated with DMSO diluent from 0-3 dpi (FIG. 3B, lanes 1-4). In contrast, VZV proteins were greatly reduced in cells treated with L-BHDU (lanes 5-8), although there was a slight but detectable increase in virus proteins at 2 dpi (lane 7). This increase was more notable for ORF4 and IE62, which do not depend on VZV DNA synthesis for induction. These trends were confirmed by densitometry to compare band intensities for ORF4, IE62, and gE to β-actin (data not shown). These results were consistent with the hypothesis that L-BHDU treatment would reduce late proteins more than immediate early and early proteins if it were acting to inhibit VZV DNA polymerase.

The cell-associated inoculum also has the potential to transfer VZV genomes, mRNA and proteins to adjacent cells by fusion or virions on the cell surface. To further examine the effects of L-BHDU on VZV protein spread, the localization of IE62 was observed by fluorescence microscopy. IE62 activates immediate-early, early, and late VZV genes (Perera et al., 1992). In a typical VZV infection, IE62 is present in the nucleus early in infection and is translocated from the nucleus to the cytoplasm at late times of infection (Kinchington and Turse, 1998; Piette et al., 1995). We hypothesized that treatment with L-BHDU would not only limit the expression of IE62 to the nucleus, but prevent its translocation to the cytoplasm that depends on phosphorylation by other viral proteins (Eisfeld et al., 2006; Kinchington et al., 2000). HFFs were infected with a cell-associated inoculum of VZV-IE62-mRFP and treated with DMSO diluent alone or 2 μM L-BHDU for 48 h. The localization of IE62-mRFP fusion protein was detected by fluorescence microscopy of live cultures in chamber slides. When VZV-infected cells were treated with DMSO diluent alone, large foci formed and IE62 was observed in the nuclei and diffusely in the cytoplasm (FIG. 3C). In L-BHDU treated cells, IE62 was in the nucleus and foci included no more than 5 infected cells (FIG. 3E). IE62 was restricted to what appeared to be inoculum as there was no indication of standard plaque formation in the phase-contrast images of the HFFs compared to the DMSO diluent alone (FIG. 3D, F). Thus L-BHDU treatment prevented IE62 amplification and translocation to the cytoplasm, and virus spread was limited to only those cells adjacent to the inoculum.

L-BHDU Prevents VZV Replication in SCID-Hu Mice

The SCID-Hu mouse model is valuable for analyzing VZV pathogenesis and potential antiviral compounds, and so it was employed to evaluate the effectiveness of L-BHDU in vivo (Ku et al., 2004; Oliver et al., 2008; Rowe et al.). SCID mice with xenografts of human fetal skin were inoculated by scarification with VZV-BAC-Luc. Virus spread in the skin implants was monitored daily by bioluminescence imaging starting at 2 dpi. When VZV infection had been established and the bioluminescence signal for an individual mouse crossed the background threshold of $2\times10^4$ total flux (usually at 2-3 dpi), the mouse was randomly assigned to either a treatment or control group (n=4 or 5). DMSO diluent and L-BHDU (8, 15, or 150 mg/kg/day) were administered by daily oral gavage, while valaciclovir (3 mg/mL) was administered in the drinking water. Representative bioluminescent images of mice from three of the treatment groups at Day 5 post infection demonstrate the presence of the bioluminescence signal directly above the infected skin implant (FIG. 4A). To monitor the changes in virus spread over the course of treatment, a region of interest (ROI) was placed over the bioluminescence signal of each mouse. The total flux values for each treatment group were averaged and graphed against the treatment day to show the VZV growth kinetics (FIG. 4B). In mice treated with DMSO diluent, virus growth was unrestricted and the bioluminescence signal increased more than 1000-fold over 7 days. Treatment with L-BHDU (15 mg/kg/day) reduced virus spread after 4 days, resulting in an approximately 10-fold reduction in bioluminescence signal by the end of the experiment. When the mice were treated with a higher dose of L-BHDU (150 mg/kg/day), virus growth was severely limited and the bioluminescence signal increased approximately 10-fold over the course of 7 days.

In previous studies using this model, the inventors found that calculating the virus growth rate for each mouse could address variability from animal to animal (Rowe et al.). Variability arises from a fresh virus inoculum for each experiment, imprecise scarification, and implant size. Hence, the net virus yield is less informative to antiviral activity than whether virus replication was inhibited. The rate of VZV spread in each skin implant was calculated from the day after treatment was initiated to the day it ended. The average VZV growth rate was then calculated for each group (FIG. 4C, Table 1). Combined data from two separate experiments demonstrate that the DMSO diluent (n=8) had no effect on the VZV growth rate, producing a rate of 0.61±0.10 $\log_{10}$ photons/s/day that exceeded the typical results in cultured HFFs of 0.50 (½ $\log_{10}$ per day). The average rate of VZV growth in the mice treated with valaciclovir (n=5) was 0.62±0.05 $\log_{10}$ photons/s/day, which is nearly identical to that of the diluent treated group, thus there was no antiviral effect. The low doses of L-BHDU (8 and 15 mg/kg/day) caused an intermediate reduction in the VZV growth rate at 0.24-0.25 $\log_{10}$ photons/s/day, and the high dose (150 mg/kg/day) almost completely prevented VZV replication and reduced the growth rate to 0.09±0.21 $\log_{10}$ photons/s/day. The differences in VZV growth rates between all doses of L-BHDU and the diluent were significant (Table 1). No overt toxicity from L-BHDU was seen in vivo. L-BHDU and DMSO both caused moderate weight loss, which did not correspond to dose, and mortality was ⅛ in the DMSO group and ⅕ in the 8 mg/kg/day L-BHDU group. The valaciclovir group lost >20% of body weight, suggesting mice were averse to the drug in water.

To determine the concentrations of L-BHDU in mouse organs and the human skin xenografts, preliminary pharmacology analysis was performed. Tissue and plasma specimens were collected two hours after the final treatment, and then drug concentrations were measured by HPLC. The maximum concentration ($C_{max}$, μg/mL of plasma or μg/g of tissue) was determined and the ratio to plasma was calculated (Table 2). L-BHDU reached similar concentrations in the mouse skin and the human skin xenografts and the levels were dose dependent. For the 150 mg/kg/day group, the amount of L-BHDU found in the skin implant was only slightly less than the concentration found in the plasma with a ratio to plasma of 0.88±0.29. Drug levels in the heart were similar to plasma, while levels in the spleen and liver were slightly higher at 1.36±0.23 and 1.47±0.30, respectively. The kidney and lung had the highest ratio to plasma. Not unexpectedly, little drug was detected in the brain. In the mice given 8 mg/kg/day L-BHDU, the concentration in the human skin implants was 0.73±0.08 μg/g, from which the approximate molar concentration of 2.3 μM can be calculated from the known molecular weight of 319.1 g/mol. This concentration is in the effective range determined in HFFs and SOC and exceeds the $EC_{50}$ by 76-fold.

Further Studies-Prodrug Forms of L-BHDU

The α-herpesvirus varicella-zoster virus (VZV) causes chicken-pox (varicella) and shingles (zoster). Current treatments are acyclovir and its derivatives, phosphonoformate, and brivudin (Europe only). Live, attenuated vaccines (Varivax, Zostavax) lower the incidence of primary and recurrent infections. Additional antiviral drugs with increased potency are needed, especially for resistant VZV strains and to treat post-herpetic neuralgia. The inventors have found that the bromovinyl uracil derivative (L-BHDU) and related prodrug forms (below) were effective against

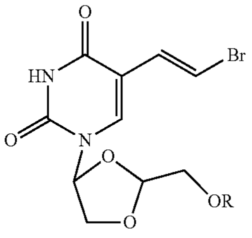

B
1. H: L-BHDU
2. Valine
3. Methylphosphoamidate
4. Ethylphosphoamidate

VZV in culture and in a mouse model, so 3 related prodrugs were evaluated for their effects on VZV-BAC-Luc replication in HFFs and skin organ culture (SOC). Virus spread was measured by bioluminescence imaging.

The ethyl- and methyl-phosphoamidate derivatives were similar to L-BHDU, with $EC_{50}$ 0.1-0.3 μM in HFF at 48 hpi.

In SOC, the $EC_{50}$ of L-BHDU and the ethyl derivatives were similar (methyl not tested). The valyl derivative was most potent, with an $EC_{50}$ of 0.038 in HFFs and 0.05 μM in SOC at 6 dpi, several fold more potent than t L-BDHU. At 2 μM, these compounds did not affect HFF proliferation, and they were nontoxic up to 200 over 3 days. HFF cells treated with these compounds (2 μM) appeared normal and VZV plaque size was reduced. Additional tests are being conducted to evaluate these compounds against VZV strains resistant to acyclovir, their effects on viral DNA synthesis, and their effectiveness in the SCID-Hu skin implant mouse model. Overall, the results indicate that L-BHDU prodrugs, especially the valyl derivative and related amino acyl derivatives, show unexpected activity and promise as novel antiviral agents for treating VZV infections, shingles and other secondary effects and/or disease states of VZV infections.

4. Discussion

The results of this study confirmed the activity of L-BHDU against VZV in cultured cells, and extended the evaluation in human skin ex vivo and engrafted in mice. L-BHDU was effective in all three systems at low micromolar concentrations, and the treatment was not toxic to cells, skin, or mice, although an exact concentration that causes 50% toxicity ($TC_{50}$) was not determined in culture. The inventors found that L-BHDU caused growth arrest but not cell lysis or death at 200 μM, thus this concentration may be near the $TC_{50}$. Using 200 μM as an approximation of the $TC_{50}$, the selective index (SI) in HFFs can be estimated as 6667 (200/0.03 μM), and could possibly be higher if future cytotoxicity assays determine a more precise $TC_{50}$. An SI of 6667 greatly exceeds the SIs for acyclovir and phosphonoacetic acid (PAA) that we determined using the same culture system as 250 and 60, respectively (Rowe et al.). These results also agree with previous studies that showed L-BHDU was 30 times more potent than acyclovir and more selective against VZV than Epstein Barr virus and herpes simplex virus types 1 and 2 (Choi et al., 2000). Therefore, L-BHDU was as effective in culture, if not more, than other drugs currently being used for treating VZV infections in the United States. In Europe, brivudin (BVDU) is used to treat HSV and VZV infections, and it has similar potency to L-BHDU in culture (De Clercq, 2005). However, the potential lethal interactions between BVDU and 5'-fluorouracil deserve caution. L-BHDU may not have this risk since early indications are that it does not produce toxic metabolites when cleaved with dihydropyrimidine dehydrogenase (Li et al., 2000). Thus L-BHDU compares well to other antivirals in selectivity and potency against VZV and may even have safety advantages.

The inventors showed that L-BHDU prevented VZV spread in culture by reducing viral DNA and protein synthesis, although questions remain about its molecular mechanism of action. L-BHDU is a substrate of VZV TK and only the monophosphate form is detected in infected cells and lysates (Li et al., 2000). L-BHDU monophosphate could inhibit the viral DNA polymerase directly, cause DNA chain termination, or reduce pools of deoxythymidine triphosphate (dTTP) by inhibiting thymidylate synthase, which is a known inhibitory mechanism of BVDU monophosphate (Balzarini et al., 1993). Further studies are necessary to discern among these possibilities. Experiments are planned to isolate VZV strains resistant to L-BHDU, map the mutations to relevant viral genes, and to test whether resistance to acyclovir and L-BHDU are linked. The effects of L-BHDU on VZV protein expression agree with its putative inhibition of DNA synthesis, since the immediate early protein ORF4 continued to be expressed at relatively higher levels than the late protein gE in the presence of the drug (full expression of gE depends on DNA replication). Moreover, inhibition of DNA polymerase by L-BHDU would not be expected to quickly block transcription and translation of luciferase that is expressed from the SV40 immediate early promoter in VZV-BAC-Luc (Zhang et al., 2007). This continued protein synthesis might give momentum to VZV spread and bioluminescence even when L-BHDU concentrations are inhibitory to viral DNA synthesis. However, the inventors found that L-BHDU limited VZV spread to 2-5 cells beyond the inoculum and bioluminescence tapered off after two days, indicating that it eventually halted virus replication. Efforts are currently underway to construct recombinant VZV strains with luciferase under control of a true late promoter, and such reporter viruses may be better for evaluating antiviral drugs like L-BHDU that are thought to inhibit DNA synthesis.

L-BHDU proved to be highly effective in skin organ culture and the estimated $EC_{50}$, <0.1 μM, was lower than the lowest dose tested. The actual $EC_{50}$ determination awaits further tests, and is likely similar to the $EC_{50}$ of 0.03-0.07 μM in culture measured in this study and by others (Choi et al., 2000; Li et al., 2000). The concordance of $EC_{50}$ in SOC and culture is another difference between L-BHDU and acyclovir. The inventors found that 400 μM acyclovir was necessary to prevent VZV spread in SOC whereas 100 μM acyclovir was required in HFFs (Rowe et al.). It is not known why acyclovir is less potent in full-thickness skin than in skin fibroblasts. This bodes well for future studies with L-BHDU, as its potency is not hampered by the increased complexity of the skin tissue. The SOC model offers several important advantages for screening potential antiviral compounds (Rowe et al.). First, SOC can be used to predict the efficacy of compounds in vivo, for if they fail to inhibit VZV ex vivo they typically fail in mice. Second, SOC can be used to estimate the effective dose for a compound in vivo, which may be somewhat higher than in culture. However, this was not the case for L-BHDU. Third, the number of replicates can be substantially higher in SOC than in mice, thus providing better statistical power. Of course, SOC is also less costly than studies using SCID-Hu mice, which require isolator caging in specialized facilities. Lastly, SOC is convenient for evaluating compounds applied topically, in a cream base or DMSO solvent, directly to the epidermal surface. BVDU and acyclovir in 95% DMSO with or without a skin permeation enhancer have been tested for the topical treatment of HSV-1 (Afouna et al., 1998), and it would be informative to evaluate L-BHDU this way since topical drugs are clinically relevant for patients suffering from zoster.

The effects of L-BHDU in vivo were not known prior to this study, and the inventors are encouraged that it was both potent and tolerated. There are several aspects of in vivo studies that deserve further investigation. Determining the L-BHDU $EC_{50}$ in the SCID-Hu mouse model may show that it is more potent than we demonstrated here at a dose of 8 mg/kg/day. It will also be important to compare L-BHDU to existing antiviral drugs. Since valaciclovir in drinking water was not an effective route of delivery in this study, an alternative method would be to administer VACV by oral gavage as was done to treat herpetic keratitis (Itahashi et al., 2008). However, VACV may not present the optimal positive control because others showed that it has little to no effect on VZV replication in SCID-Hu mice (Oliver et al., 2008). Perhaps brivudin or Foscarnet would be preferable, as we previously reported that 36 mg/kg/day phosphonoacetic acid (PAA) administered subcutaneously from osmotic pumps significantly reduced VZV growth in this model (Rowe et al.).

The SCID-Hu mouse model will be useful to address more questions regarding L-BHDU in vivo, such as the timing of the treatment with respect to infection, drug preparations, and routes of administration. The rationale in this study was to mimic natural infection, thus VZV infection was established before treatment commenced. The inventors have found that treating earlier than 2 dpi confounds the data analysis, as one cannot distinguish between failure of the virus inoculum to infect the implant or virus infection prevented by an effective compound. Starting L-BHDU treatment before VZV infection, or simultaneously, would likely improve the drug efficacy, but this approach is less likely to provide data with clinical relevance. Future evaluations of L-BHDU should compare its efficacy in preparations other than DMSO, such as suspension in carboxymethylcellulose for oral delivery, or in oil-based creams for topical delivery. Drug absorption by these routes can be measured by sampling mouse skin, since we found that the $C_{max}$ of L-BHDU in mouse skin was comparable to the levels in human skin implants. Interestingly, the 8 mg/kg/day dose of L-BHDU in this study produced a $C_{max}$ of approximately 0.7 μg/g (human skin), which is similar to the brivudin $C_{max}$ of 1.7 μg/mL (plasma) in herpes zoster patients given a dose of 125 mg/day (Keam et al., 2004). Thus these related uridine analogues might have similar antiviral potency in vivo.

REFERENCES

Afouna, M. I., Mehta, S.C., Ghanem, A. H., Higuchi, W. I., Kern, E. R., De Clercq, E., and El-Shattawy, H. H. (1998). Assessment of correlation between skin target site free drug concentration and the in vivo topical antiviral efficacy in hairless mice for (E)-5-(2-bromovinyl)-2'-deoxyuridine and acyclovir formulations. J Pharm Sci 87(8), 917-21.

Ahmed, A. M., Brantley, J. S., Madkan, V., Mendoza, N., and Tyring, S. K. (2007). Managing herpes zoster in immunocompromised patients. Herpes 14(2), 32-6.

Andrei, G., Snoeck, R., Reymen, D., Liesnard, C., Goubau, P., Desmyter, J., and De Clercq, E. (1995). Comparative activity of selected antiviral compounds against clinical isolates of varicella-zoster virus. Eur J Clin Microbiol Infect Dis 14(4), 318-29.

Babich, H., Sedletcaia, A., and Kenigsberg, B. (2002). In vitro cytotoxicity of protocatechuic acid to cultured human cells from oral tissue: involvement in oxidative stress. Pharmacol Toxicol 91(5), 245-53.

Balzarini, J., Bohman, C., and De Clercq, E. (1993). Differential mechanism of cytostatic effect of (E)-5-(2-bromovinyl)-2'-deoxyuridine, 9-(1,3-dihydroxy-2-propoxymethyl)guanine, and other antiherpetic drugs on tumor cells transfected by the thymidine kinase gene of herpes simplex virus type 1 or type 2. J Biol Chem 268(9), 6332-7.

Bednarski, K., Dixit, D., Wang, W., Evans, C., Jin, H., Yuen, L., and Mansour, T. (1994). Inhibitory activities of herpes simplex viruses type 1 and 2 and human cytomegalovirus by stereoisomers of 2'-deoxy-3'-oxa-5(E)-2-bromovinyl) uridines and their 4'-thio analogues. Bioorg Med Chem Lett 4(2), 2667-2672.

Choi, Y., Li, L., Grill, S., Gullen, E., Lee, C. S., Gumina, G., Tsujii, E., Cheng, Y. C., and Chu, C. K. (2000). Structure-activity relationships of (E)-5-(2-bromovinyl)uracil and related pyrimidine nucleosides as antiviral agents for herpes viruses. J Med Chem 43(13), 2538-46.

Chu, C. K., Ma, T., Shanmuganathan, K., Wang, C., Xiang, Y., Pai, S. B., Yao, G. Q., Sommadossi, J. P., and Cheng, Y. C. (1995). Use of 2'-fluoro-5-methyl-beta-L-arabinofuranosyluracil as a novel antiviral agent for hepatitis B virus and Epstein-Barr virus. Antimicrob Agents Chemother 39(4), 979-81.

Cohen, J. I., Straus, S. E., and Arvin, A. M. (2007). Varicella-zoster virus replication, pathogenesis, and management. 5th ed. In “Fields Virology” (D. M. Knipe, P. M. Howley, D. E. Griffin, R. A. Lamb, M. A. Martin, B. Roizman, and S. E. Straus, Eds.), Vol. 2, pp. 2773-2818. 2 vols. Lippincott-Williams and Wilkens, Philadelphia.

De Clercq, E., Descamps, J., De Somer, P., Barr, P. J., Jones, A. S., and Walker, R. T. (1979). (E)-5-(2-Bromovinyl)-2'-deoxyuridine: a potent and selective anti-herpes agent. Proc Natl Acad Sci USA 76(6), 2947-51.

De Clercq, E. (2004). Antiviral drugs in current clinical use. J Clin Virol 30(2), 115-33.

De Clercq, E. (2005). Recent highlights in the development of new antiviral drugs. Current Opinion in Microbiology 8(5), 552-60.

Diasio, R. B. (1998). Sorivudine and 5-fluorouracil; a clinically significant drug-drug interaction due to inhibition of dihydropyrimidine dehydrogenase. Br J Clin Pharmacol 46(1), 1-4.

Eisfeld, A. J., Turse, S. E., Jackson, S. A., Lerner, E. C., and Kinchington, P. R. (2006). Phosphorylation of the varicella-zoster virus (VZV) major transcriptional regulatory protein IE62 by the VZV open reading frame 66 protein kinase. J Virol 80(4), 1710-23.

Holcomb, K., and Weinberg, J. M. (2006). A novel vaccine (Zostavax) to prevent herpes zoster and postherpetic neuralgia. J Drugs Dermatol 5(9), 863-6.

Keam, S. J., Chapman, T. M., and Figgitt, D. P. (2004). Brivudin (bromovinyl deoxyuridine). Drugs 64(18), 2091-7; discussion 2098-9.

Keizer, H. J., De Bruijn, E. A., Tjaden, U. R., and De Clercq, E. (1994). Inhibition of fluorouracil catabolism in cancer patients by the antiviral agent (E)-5-(2-bromovinyl)-2'-deoxyuridine. J Cancer Res Clin Oncol 120(9), 545-9.

Kinchington, P. R., and Turse, S. E. (1998). Regulated nuclear localization of the varicella-zoster virus major regulatory protein, IE62. J Infect Dis 178 Suppl 1, S16-21.

Kinchington, P. R., Fite, K., and Turse, S. E. (2000). Nuclear Accumulation of IE62, the Varicella-Zoster Virus (VZV) Major Transcriptional Regulatory Protein, Is Inhibited by Phosphorylation Mediated by the VZV Open Reading Frame 66 Protein Kinase. J. Virol. 74(5), 2265-2277.

Ku, C. C., Zerboni, L., Ito, H., Graham, B. S., Wallace, M., and Arvin, A. M. (2004). Varicella-zoster virus transfer to skin by T Cells and modulation of viral replication by epidermal cell interferon-alpha. J Exp Med 200(7), 917-25.

Leisenfelder, S. A., and Moffat, J. F. (2006). Varicella-zoster virus infection of human foreskin fibroblast cells results in atypical cyclin expression and cyclin-dependent kinase activity. J Virol 80(11), 5577-87.

Li, L., Dutschman, G. E., Gullen, E. A., Tsujii, E., Grill, S. P., Choi, Y., Chu, C. K., and Cheng, Y. C. (2000). Metabolism and mode of inhibition of varicella-zoster virus by L-beta-5-bromovinyl-(2-hydroxymethyl)-(1,3-dioxolanyl)uracil is dependent on viral thymidine kinase. Mol Pharmacol 58(5), 1109-14.

Moffat, J. F., Stein, M. D., Kaneshima, H., and Arvin, A. M. (1995). Tropism of varicella-zoster virus for human CD4+ and CD8+ T lymphocytes and epidermal cells in SCID-hu mice. Journal of Virology 69(9), 5236-42.

Moffat, J. F., and Arvin, A. M. (1999). Varicella-zoster virus infection of T cells and skin in the SCID-hu mouse model. In “Handbook of Animal Models of Infection” (0. Zak, and M. A. Sande, Eds.), pp. 973-980. Academic Press, San Diego.

Oliver, S. L., Zerboni, L., Sommer, M., Rajamani, J., and Arvin, A. M. (2008). Development of recombinant varicella-zoster viruses expressing luciferase fusion proteins for live in vivo imaging in human skin and dorsal root ganglia xenografts. J Virol Methods 154(1-2), 182-93.

Oxman, M. N., Levin, M. J., Johnson, G. R., Schmader, K. E., Straus, S. E., Gelb, L. D., Arbeit, R. D., Simberkoff, M. S., Gershon, A. A., Davis, L. E., Weinberg, A., Boardman, K. D., Williams, H. M., Zhang, J. H., Peduzzi, P. N., Beisel, C. E., Morrison, V. A., Guatelli, J. C., Brooks, P. A., Kauffman, C. A., Pachucki, C. T., Neuzil, K. M., Betts, R. F., Wright, P. F., Griffin, M. R., Brunell, P., Soto, N. E., Marques, A. R., Keay, S. K., Goodman, R. P., Cotton, D. J., Gnann, J. W., Jr., Loutit, J., Holodniy, M., Keitel, W. A., Crawford, G. E., Yeh, S. S., Lobo, Z., Toney, J. F., Greenberg, R. N., Keller, P. M., Harbecke, R., Hayward, A. R., Irwin, M. R., Kyriakides, T. C., Chan, C. Y., Chan, I. S., Wang, W. W., Annunziato, P. W., and Silber, J. L. (2005). A vaccine to prevent herpes zoster and postherpetic neuralgia in older adults. N Engl J Med 352(22), 2271-84.

Perera, L. P., Mosca, J. D., Sadeghi-Zadeh, M., Ruyechan, W. T., and Hay, J. (1992). The varicella-zoster virus immediate early protein, IE62, can positively regulate its cognate promoter. Virology 191(1), 346-54.

Piette, J., Defechereux, P., Baudoux, L., Debrus, S., Merville, M. P., and Rentier, B. (1995).

Varicella-zoster virus gene regulation. Neurology 45(12 Suppl 8), S23-7.

Repetto, G., del Peso, A., and Zurita, J. L. (2008). Neutral red uptake assay for the estimation Of cell viability/cytotoxicity. Nat Protoc 3(7), 1125-31.

Rowe, J., Greenblatt, R. J., Liu, D., and Moffat, J. F. Compounds that target host cell proteins prevent varicella-zoster virus replication in culture, ex vivo, and in SCID-Hu mice. Antiviral Res.

Sampathkumar, P., Drage, L. A., and Martin, D. P. (2009). Herpes zoster (shingles) and postherpetic neuralgia. Mayo Clin Proc 84(3), 274-80.

Seward, J. F., Marin, M., and Vazquez, M. (2008). Varicella vaccine effectiveness in the US vaccination program: a review. J Infect Dis 197 Suppl 2, S82-9.

Sexton, C. J., Naysaria, H. A., Leigh, I. M., and Powell, K. (1992). Replication of varicella zoster virus in primary human keratinocytes. J Med Virol 38(4), 260-4.

Shigeta, S., Yokota, T., Iwabuchi, T., Baba, M., Konno, K., Ogata, M., and De Clercq, E. (1983). Comparative efficacy of antiherpes drugs against various strains of varicella-zoster virus. J Infect Dis 147(3), 576-84.

Spadari, S., Maga, G., Focher, F., $C_1$-arrocchi, G., Manservigi, R., Arcamone, F., Capobianco, M., Carcuro, A., Colonna, F., Iotti, S., and et al. (1992). L-thymidine is phosphorylated by herpes simplex virus type 1 thymidine kinase and inhibits viral growth. J Med Chem 35(22), 4214-20.

Taylor, S. L., Kinchington, P. R., Brooks, A., and Moffat, J. F. (2004). Roscovitine, a cyclin dependent kinase inhibitor, prevents replication of varicella-zoster virus. Journal of Virology 78(6), 2853-2862.

Taylor, S. L., and Moffat, J. F. (2005). Replication of varicella-zoster virus in human skin organ culture. J Virol 79(17), 11501-6.

Vazquez, M., LaRussa, P. S., Gershon, A. A., Niccolai, L. M., Muehlenbein, C. E., Steinberg, S. P., and Shapiro, E. D. (2004). Effectiveness over time of varicella vaccine. Jama 291(7), 851-5.

Zhang, Z., Rowe, J., Wang, W., Sommer, M., Arvin, A., Moffat, J., and Zhu, H. (2007). Genetic analysis of varicella-zoster virus ORFO to ORF4 by use of a novel luciferase bacterial artificial chromosome system. J Virol 81(17), 9024-33.

The invention claimed is:

1. An L-nucleoside compound according to the chemical structure:

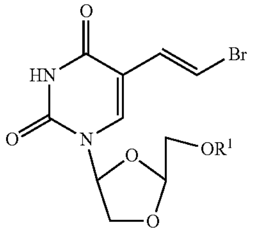

1

Where $R^1$ is an amino acyl group derived from an amino acid or a phosphoamidate group according to the chemical structure:

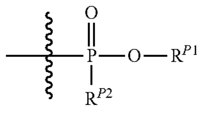

Where $R^{P1}$ is a $C_1$-$C_{20}$ linear, branched or cyclic alkyl group, or an optionally substituted aryl, heteroaryl or heterocyclic group; and $R^{P2}$ is a —$NR^{N1}R^{N2}$ group or a B' group;

Where $R^{N1}$ and $R^{N2}$ are each independently H or a $C_1$-$C_{20}$ alkyl group, an optionally substituted phenyl group, heteroaryl or heterocyclic group; and B' is a

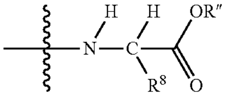

group;

Where $R^8$ is sidechain of an amino acid, and

R" is a $C_1$ to $C_{20}$ linear, branched or cyclic alkyl group, an aryl group, heteroaryl group or heterocyclic group, each of which group is optionally substituted, or a pharmaceutically acceptable salt, anomer, solvate or polymorph thereof.

2. The compound according to claim 1 wherein $R^1$ is an amino acyl group derived from a L-α-amino acid.

3. The compound according to claim 2 wherein said L-α-amino acid is selected from the group consisting of alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

4. The compound according to claim 3 wherein said L-α-amino acid is selected from the group consisting of valine, phenylalanine, leucine, isoleucine, threonine, alanine or glycine.

5. The compound according to claim 1 wherein said amino acyl group is derived from L-valine.

6. The compound according to claim 1 wherein $R^1$ is a phosphoamidate group, $R^{P1}$ is a $C_8$-$C_{20}$ alkyl group or an optionally substituted aryl or heteroaryl group.

7. The compound according to claim 6 wherein said optionally substituted aryl group is a phenyl, benzyl or naphthyl group.

8. The compound according to claim 6 wherein said optionally substituted heteroaryl group is a pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine, pyridopyrimidine, thiophene, benzothiophene, furan, pyran, cyclopentapyran, benzofuran, isobenzofuran, thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole.

9. The compound according to claim 1 wherein $R^{P2}$ is a —$NR^{N1}R^{N2}$ group where $R^{N1}$ and $R^{N2}$ are independently H, a $C_1$-$C_{20}$ alkyl group or an optionally substituted aryl group.

10. The compound according to claim 9 wherein $R^{N1}$ and $R^{N2}$ are both H.

11. The compound according to claim 9 wherein $R^{N1}$ is H and $R^{N2}$ is a $C_8$-$C_{20}$ alkyl group, a phenyl group or a benzyl group.

12. The compound to claim 1 wherein $R^1$ is a phosphoamidate group, $R^{P1}$ is a $C_1$-$C_{20}$ alkyl group and $R^{P2}$ is a B' group

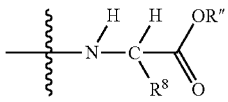

wherein $R^8$ is sidechain of an L-α-amino acid selected from the group consisting of alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan and tyrosine and R" is a $C_1$ to $C_{20}$ linear, branched or cyclic alkyl group.

13. The compound according to claim 12 wherein said amino acid is selected from the group consisting of valine, phenylalanine, leucine, isoleucine, threonine, alanine and glycine.

14. The compound according to claim 12 wherein said amino acid is selected from the group consisting of valine, phenylalanine, leucine, isoleucine and threonine.

15. The compound according to claim 1 which is

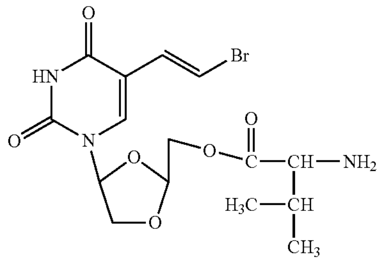 [SMILES: CC(C)C(N)C(=O)OCC1OCC(n2cc(/C=C/Br)c(=O)[nH]c2=O)O1]

or a diastereomer or pharmaceutically acceptable salt thereof.

16. A pharmaceutical composition comprising an effective amount of a compound according to claim 1 in combination with a pharmaceutically acceptable carrier, additive or excipient.

17. A method of treating a VZV infection in a patient in need thereof comprising administering to said patient an effective amount of a compound according to claim 1.

18. A method of inhibiting or reducing the likelihood of a secondary disease state or condition of VZV in a patient at risk comprising administering to said patient an effective amount of a compound according to claim 1.

19. The method according to claim 18 wherein said second disease state or condition is a skin rash or post-herpetic neuralgia.

20. A method of reducing the likelihood of or treating shingles in a patient in need comprising administering to said patient an effective amount of a compound according to claim 1 to said patient.

21. The method according to claim 17 wherein said compound is combined with an effective amount of a compound selected from the group consisting of acyclovir (ACV), valaciclovir (VACV), penciclovir (PCV) and famciclovir (FCV), phosphonoformate, idoxuridine, trifluridine, brivudin and mixtures thereof.

22. The method according to claim 18 wherein said compound is combined with an effective amount of a compound selected from the group consisting of acyclovir (ACV), valaciclovir (VACV), penciclovir (PCV) and famciclovir (FCV), phosphonoformate, idoxuridine, trifluridine, brivudin and mixtures thereof.

23. The pharmaceutical composition according to claim 16 in combination with an effective amount of an antiviral agent selected from the group consisting of acyclovir (ACV), valaciclovir (VACV), penciclovir (PCV) and famciclovir (FCV), phosphonoformate, idoxuridine, trifluridine, brivudin and mixtures thereof.

* * * * *